(12) United States Patent
Shaw et al.

(10) Patent No.: US 11,433,116 B2
(45) Date of Patent: Sep. 6, 2022

(54) GJA1 ISOFORMS PROTECT AGAINST METABOLIC STRESS

(71) Applicant: Cedars-Sinai Medical Center, Los Angeles, CA (US)

(72) Inventors: Robin Shaw, Los Angeles, CA (US); TingTing Hong, Santa Monica, CA (US); Ying Fu, Los Angeles, CA (US); Shaohua Xiao, Los Angeles, CA (US); Wassim Basheer, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 387 days.

(21) Appl. No.: 16/089,890

(22) PCT Filed: Apr. 13, 2017

(86) PCT No.: PCT/US2017/027457
§ 371 (c)(1),
(2) Date: Sep. 28, 2018

(87) PCT Pub. No.: WO2017/180896
PCT Pub. Date: Oct. 19, 2017

(65) Prior Publication Data
US 2019/0117729 A1    Apr. 25, 2019

Related U.S. Application Data

(60) Provisional application No. 62/322,630, filed on Apr. 14, 2016.

(51) Int. Cl.
*A61K 38/00* (2006.01)
*A61K 38/17* (2006.01)
*C07K 14/705* (2006.01)
*C07K 14/47* (2006.01)
*A61P 9/10* (2006.01)
*A61P 9/04* (2006.01)

(52) U.S. Cl.
CPC .......... *A61K 38/1709* (2013.01); *A61K 38/00* (2013.01); *A61K 38/17* (2013.01); *A61K 38/177* (2013.01); *A61P 9/04* (2018.01); *A61P 9/10* (2018.01); *C07K 14/47* (2013.01); *C07K 14/705* (2013.01)

(58) Field of Classification Search
CPC .... A61K 38/1709; A61K 38/17; A61K 38/00; A61K 38/177; A61P 9/04; A61P 9/10; C07K 14/47; C07K 14/705
See application file for complete search history.

(56) References Cited

U.S. PATENT DOCUMENTS

| | | |
|---|---|---|
| 7,153,822 B2 | 12/2006 | Jensen et al. |
| 2005/0014262 A1 | 1/2005 | Gao et al. |
| 2008/0095819 A1 * | 4/2008 | Gourdie ............ A61P 9/00 424/423 |
| 2010/0189701 A1 | 7/2010 | Cohen et al. |
| 2014/0235526 A1 | 8/2014 | Srivastava et al. |
| 2015/0140060 A1 | 5/2015 | Ghatnekar |
| 2015/0174196 A1 | 6/2015 | Gourdie et al. |

FOREIGN PATENT DOCUMENTS

| | | | |
|---|---|---|---|
| WO | WO-2006134494 A2 * | 12/2006 | ............ A61P 1/04 |
| WO | 2017180896 A1 | 10/2017 | |

OTHER PUBLICATIONS

Smyth et al Cell reports 2-13, 5, 3, 611-618 (Year: 2013).*
Liaw et al . Emerging therapies in acute ischemic stroke [version 1; peer review. F1000Research 2020, 9(F1000 Faculty Rev. 2020. (Year: 2020).*
Collao et al. Front. Cell Dev. Biol., Jan. 28, 2020), Role of Metabolic Stress and Exercise in Regulating Fibro/Adipogenic Progenitors (Year: 2020).*
Schulz et al. Connexin 43 is an emerging therapeutic target in ischemia/ reperfusion injury, cardioprotection and neuroprotection. 2015. Pharmacol Ther. Sep. 2015 ; 153: 90-106 (Year: 2015).*
Smyth et al. Autoregulation of connexin43 gap junction formation by internally translated isoforms. Cell Rep. Nov. 14, 2013; 5(3): 611-618 (Year: 2013).*
White et al. Role of Metabolic Stress Responses of Apoptosis and Autophagy in Tumor Suppression. 2010. Ernst Schering Found Symp Proc. 2007; (4): 23-34 (Year: 2010).*
Sivanos et al. The modulatory effects of connexin 43 on cell death/survival beyond cell coupling. Progress in Biophysics and Molecular Biology vol. 94, Issues 1-2, May-Jun. 2007, pp. 219-232 (Year: 2007).*
International Search Report and Written Opinion of PCT/US2017/027457, dated Jul. 12, 2017, 12 Pages.
Basheer et al., The "Tail" of Connexin43: An Unexpected Journey from Alternative Translation to Trafficking, 2015, Biochim Biophys Acta., 9 Pages.
Rodriguez-Sinovas et al., Translocation of Connexin 43 to the Inner Mitochondrial Membrane of Cardiomyocytes through the Heat Shock Protein 90-Dependent TOM Pathway and Its Importance for Cardioprotecdtion, 2006, Circulation Research, vol. 99(1), pp. 93-101.
Schulz et al., Connexin 43 is an Emerging Therapeutic Target in Ischemia/Reperfusion Injury, Cardioprotection and Neuroprotection, 2015, Pharmacol & Ther., vol. 153, pp. 90-106.
Smyth et al., Autoregulation of Connexin43 Gap Junction Formation by Internally Translated Isoforms, 2013, Cell Rep., vol. 5, pp. 611-618.

* cited by examiner

*Primary Examiner* — Aradhana Sasan
*Assistant Examiner* — Mercy H Sabila
(74) *Attorney, Agent, or Firm* — Linda B. Huber; Nixon Peabody LLP

(57) ABSTRACT

The present invention describes methods of treating, preventing, reducing the likelihood of having, reducing the severity of and/or slowing the progression of a medical condition related to ischemia/reperfusion in a subject using GJA1-20k as a therapeutic agent. The invention further provides a method of protecting a cell from metabolic stress, using GJA1-20k. The invention also provides for a composition and/or gene expression vector comprising GJA1-20k.

13 Claims, 10 Drawing Sheets

Specification includes a Sequence Listing.

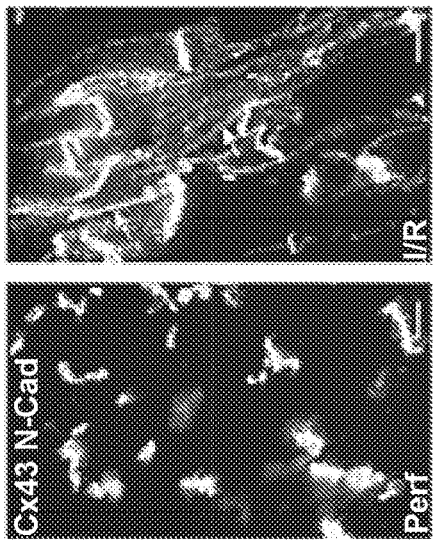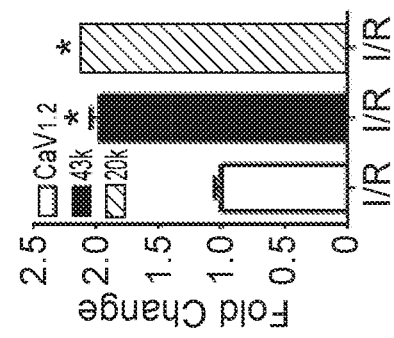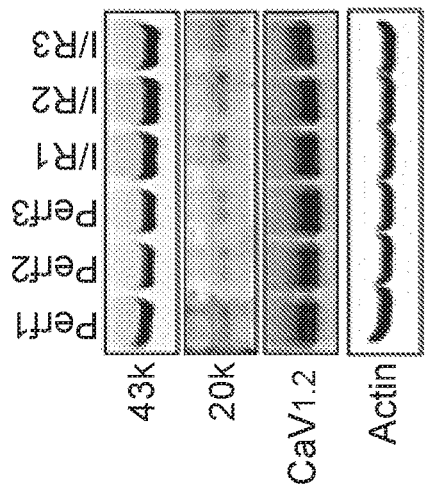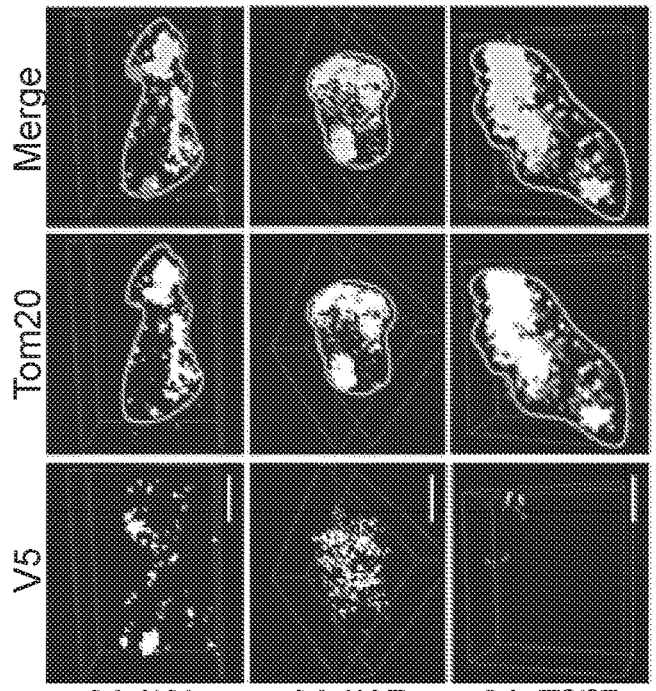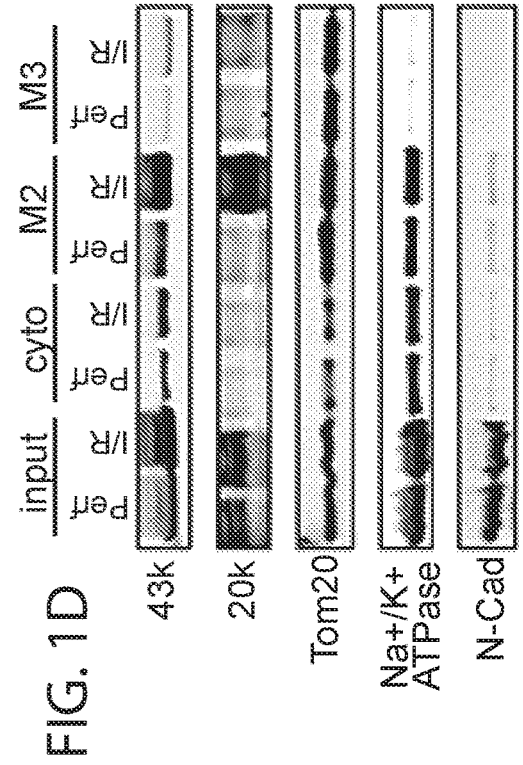

GJA1-20k
MLVVSLVSLALNIIELFYVFFKGVKDRVKGKSDPYHAT
SGALSPAKDCGSQKYAYFNGCSSPTAPLSPMSPPGY
KLVTGDRNNSSCRNYNKQASEQNWANYSAEQNRMG
QAGSTISNSHAQPFDFPDDNQNSKKLAAGHELQPLAI
VDQRPSSRASSRASSRPRPDDLEI

GJA1-11k
MSPPGYKLVTGDRNNSSCRNYNKQASEQNWANYS
AEQNRMGQAGSTISNSHAQPFDFPDDNQNSKKLAAG
HELQPLAIVDQRPSSRASSRASSRPRPDDLEI

GJA1 ISOFORMS PROTECT AGAINST METABOLIC STRESS

CROSS-REFERENCE TO RELATED APPLICATIONS

This application is a National Phase of International Application No. PCT/US2017/027457 filed Apr. 13, 2017, currently pending, which designated the U.S. and that International Application was published under PCT Article 21(2) in English, which also includes a claim of priority under 35 U.S.C. § 119(e) to U.S. provisional patent application No. 62/322,630 filed Apr. 14, 2016, the entirety of which is hereby incorporated by reference.

STATEMENT REGARDING FEDERALLY SPONSORED RESEARCH OR DEVELOPMENT

This invention was made with government support under Grant Nos. HL094414, HL109075, and HL133286 awarded by the National Institutes of Health. The government has certain rights in the invention.

FIELD OF THE INVENTION

The invention relates to medicine.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Precise Cx43 gap junction formation and localization are critical for intercellular communication; alternations of which lead to heart disease and sudden cardiac death. Cx43 also has important non-canonical roles in cell survival and ischemic injury protection, but the underlying mechanisms are not well understood. Recently, it was found that N-terminally truncated Cx43 isoforms exist endogenously in the heart, and that they are produced by alternative translation of the GJA1 mRNA. The most abundant isoform, named GJA1-20k, is required for Cx43 trafficking and gap junction formation. As trafficking of Cx43 is impaired in failing hearts, we explored GJA1-20k function during ischemia/reperfusion (I/R) injury.

In this invention, we provide compositions, methods and kits for treating various ischemia-related conditions.

SUMMARY OF THE INVENTION

Various embodiments of the present invention provide for a method of treating, preventing, reducing the likelihood of having, reducing the severity of and/or slowing the progression of a condition in a subject. The method comprising providing a GJA1-20k polypeptide or a functional variant or fragment thereof; and administering a therapeutically effective amount of the GJA1-20k polypeptide or the functional variant or fragment thereof to the subject, thereby treating, preventing, reducing the likelihood of having, reducing the severity of and/or slowing the progression of the condition in the subject.

In various embodiments, the condition is metabolic stress, ischemia, reperfusion injury, myocardial infarction, open heart surgery, cardiopulmonary bypass, coronary artery reperfusion, stroke, ischemic stroke, or nephrotoxicity, or a combination thereof.

In some embodiments, the administration of the GJA1-20k polypeptide or a functional variant or fragment thereof results in a cardioprotective effect. In other embodiments, the cardioprotective effect comprises a reduction in basal mitochondrial dependent oxygen consumption and maximal respiratory capacity.

Various embodiments of the present invention also provide for a method of treating, preventing, reducing the likelihood of having, reducing the severity of and/or slowing the progression of a condition in a subject. The method comprising providing a gene expression vector comprising a sequence of a GJA1-20k polypeptide or a functional variant or fragment thereof, wherein the gene expression vector is configured for expressing the GJA1-20k polypeptide or the functional variant or fragment thereof; and administering a therapeutically effective amount of the gene expression vector to the subject, thereby treating, preventing, reducing the likelihood of having, reducing the severity of and/or slowing the progression of the condition in the subject.

In various embodiments, the administration of the GJA1-20k polypeptide or a functional variant or fragment thereof results in a cardioprotective effect. In other embodiments, the cardioprotective effect comprises a reduction in basal mitochondrial dependent oxygen consumption and maximal respiratory capacity.

Various embodiments of the present invention also provide for a method of protecting a cell from metabolic stress, comprising: providing a GJA1-20k polypeptide or a functional variant or fragment thereof; and contacting the cell with the GJA1-20k polypeptide or the functional variant or fragment thereof, thereby protecting the cell from metabolic stress. In various embodiments, the administration of the GJA1-20k polypeptide or a functional variant or fragment thereof results in a reduction in basal mitochondrial dependent oxygen consumption and maximal respiratory capacity.

Various embodiments of the present invention also provide for a method of protecting a cell from metabolic stress, comprising: providing a gene expression vector comprising a sequence of a GJA1-20k polypeptide or a functional variant or fragment thereof, wherein the gene expression vector is configured for expressing the GJA1-20k polypeptide or the functional variant or fragment thereof; and contacting the cell with gene expression vector, thereby protecting the cell from metabolic stress. In various embodiments, the administration of the GJA1-20k polypeptide or a functional variant or fragment thereof results in a reduction in basal mitochondrial dependent oxygen consumption and maximal respiratory capacity.

Various embodiments of the present invention also provide for a composition comprising a GJA1 polypeptide or a functional variant or fragment thereof. In various embodiments, the functional variant is a variant with conservative amino acid substitutions. In some embodiments, the GJA1 polypeptide is fused to a cell penetrating peptide (CPP). In other embodiments, the GJA1 polypeptide is covalently or non-covalently conjugated to a cell penetrating peptide. In yet other embodiments, the GJA1 polypeptide is GJA1-32k, GJA1-29k, GJA1-26k, GJA1-20k, GJA1-11k, or GJA1-7k, or a functional variant or fragment thereof. In some embodiments, the GJA1-32k, GJA1-29k, GJA1-26k, GJA1-20k, GJA1-11k, or GJA1-7k, or the functional variant or fragment thereof is fused to a cell penetrating peptide (CPP).

Various embodiments of the present invention also provide for a gene expression vector comprising a sequence of a GJA1 polypeptide or a functional variant or fragment thereof, wherein the gene expression vector is configured for expressing the GJA1 polypeptide or the functional variant or fragment thereof.

In various embodiments, the gene expression vector is a viral vector, adeno-associated virus (AAV) vector, recombinant AAV (rAAV) vector, single-stranded AAV vector, double-stranded AAV vector, or self-complementary AAV (scAAV) vector, or a combination thereof. In some embodiments, the gene expression vector is a polynucleotide or a virus particle. In other embodiments, the serotype of the virus particle is AAV1, AAV2, AAV3, AAV4, AAV5, AAV6, AAV7, AAV8, AAV9, AAV10, AAV11, or AAV12, or a hybrid serotype thereof. In yet other embodiments, the GJA1 polypeptide or the functional variant or fragment thereof is fused to a cell penetrating peptide.

BRIEF DESCRIPTION OF THE DRAWINGS

Exemplary embodiments are illustrated in referenced figures. It is intended that the embodiments and figures disclosed herein are to be considered illustrative rather than restrictive.

FIGS. 1A-1I depict, in accordance with various embodiments of the invention, I/R induces GJA1-20k, which associates with mitochondria and increases cardiomyocyte survival. (FIG. 1A) Cx43 and GJA1-20k increase with cardiac ischemia/reperfusion (I/R) as compared to perfused hearts (Perf), quantified in (FIG. 1B). (FIG. 1C) Intracellular and lateralized Cx43 (arrows, away from N-cadherin) increase with I/R. Maximum intensity projections of 12.5 µm z-stacks, scale bar=10 µm. (FIG. 1D) Isoform enrichment in cytoplasmic (cyto) versus ultracentrifuged fractions (M2, M3) in perfused and I/R hearts. Tom20 marks mitochondrial content. $Na^+/K^+$ ATPase and N-cadherin mark sarcolemmal content. (FIG. 1E) 3-D STORM images of isolated mitochondria from transduced adult cardiomyocytes. Tom20 is used to outline each mitochondrion, scale bar=0.5 µm. (FIG. 1F and FIG. 1G) Exogenous GJA1-20k increases mitotracker intensity at the cardiomyocyte periphery upon $H_2O_2$ treatment. Maximum intensity projections of 12.5 µm z-stacks, scale bar=10 µm. (FIG. 1H and FIG. 1I) GJA1-20k increases cardiomyocyte survival and viability. All data are presented as the mean±s.e.m., *p<0.05, by one- or two-way ANOVA followed by comparisons between groups.

(FIG. 2A) Live confocal images of HeLa cells expressing GJA1 isoforms and mitochondrial markers (mito-BFP). GJA1-43k occasionally associates with mitochondria as small puncta (arrows). GJA1-20k colocalizes with mito-BFP and voltage-sensitive TMRM. Scale bar=5 µm. (FIG. 2B) Relative enrichment of HA-tagged isoforms in cell lysate (input), cytoplasm (cyto), and ultracentrifuged fractions (F1-F3), with progressive increase in mitochondrial (Tom20) but not plasma membrane ($Na^+K^+$ ATPase, N-Cad) content.

(FIG. 3A) Mitochondrial morphology and distribution (Tom20 immunofluorescence) in HeLa cells expressing GFP-tagged GST, GJA1-43k, or GJA1-20k, treated with PBS or 300 µM $H_2O_2$. Cell borders marked by GFP are outlined (dashed line). A single focal plane is shown, scale bar=5 µm. (FIG. 3B) Tom20 fluorescence density ratio within the cell periphery versus the cell center. (FIG. 3C) Quantification of cells with elongated mitochondria. (FIG. 3D) TEM and immunogold images of mitochondria (arrowheads) and microtubules (arrows) in GST-GFP versus GJA1-20k-GFP cells. GJA1-20k-GFP is detected at the mitochondrial and microtubule interface (yellow arrows). Scale bar=0.5 µm. All data are presented as the mean±s.e.m. *p<0.05, ***p<0.001, by two-way ANOVA followed by comparisons between groups.

(FIG. 4A) Six microtubule-interacting residues (Bold—"RV" and "YHAT") were removed to generate GJA1-20k-del6 (SEQ ID NO: 5). The microtubule-binding domain is underlined (SEQ ID NO: 4). Internal translational start sites are depicted as M with white fill. (FIG. 4B) Live confocal images of HeLa cells expressing GJA1-20k or GJA1-20k-del6, and mito-BFP. Scale bar=5 µm. (FIG. 4C) Tom20 fluorescence density ratio within the cell periphery versus the cell center. (FIG. 4D) Quantification of cells with elongated mitochondria. (FIG. 4E) Representative mitochondrion (mito-BFP) tracks in HeLa cells expressing GST +DMSO, GST +25 µM nocodazole (Noc), GJA1-20k +DMSO, or GJA1-20k-del6+DMSO. (FIG. 4F and FIG. 4G) Mean track velocity and maximal net displacement of individual mitochondrion. (FIG. 4H) Nonlinear Gaussian fitting of track velocity frequency and distribution. All data are presented as the mean±s.e.m., p<0.01, **p<0.0001, by two-way ANOVA followed by comparisons between groups.

(FIG. 6A) Schematic of GJA1-20k administration by AAV9-medicated gene transfer using retro-orbital injection four weeks before the ischemic insult. (FIGS. 6B and 6C) GJA1-20k, but not full length GJA1-43k, protects the heart.

(FIG. 7A) Oxygen Consumption Rate (OCR) over time after administration of GST-GFP, GJA1-20k, and GJA1-43k. (FIG. 7B) Basal mitochondria-dependent oxygen consumption rate (OCR) and maximal respiratory capacity are markedly reduced by GJA1-20k, unlike GFP or GJA1-43k controls.

DETAILED DESCRIPTION OF THE INVENTION

Figure 1F:
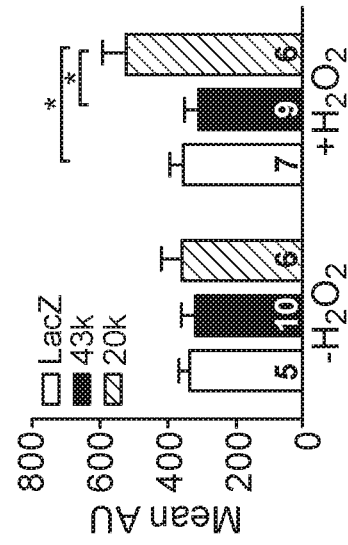

All references cited herein are incorporated by reference in their entirety as though fully set forth. Unless defined otherwise, technical and scientific terms used herein have the same meaning as commonly understood by one of ordinary skill in the art to which this invention belongs.

Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture andre tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162): 323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of ischemia, delay or slowing of ischemia, and amelioration or palliation of symptoms associated with ischemia.

"Diseases", "conditions" and "disease conditions," as used herein may include, but are in no way limited to any form of metabolic stress or metabolic stress-related condition, disease or disorder (e.g., ischemia and reperfusion injury in heart and brain).

"Contacting" as used here with reference to contacting a cell with an agent (e.g., a GJA1 polypeptide) refers to any method that is suitable for placing the agent on, in or adjacent to a target cell. For example, when the cells are in vitro, contact the cells with the agent can comprise adding the agent to culture medium containing the cells. For example, when the cells are in vivo, contacting the cells with the agent can comprise administering the agent to the subject.

As used herein, the term "administering," refers to the placement of an agent or a composition as disclosed herein into a subject by a method or route which results in at least partial localization of the agents or composition at a desired site. "Route of administration" may refer to any administration pathway known in the art, including but not limited to oral, topical, aerosol, nasal, via inhalation, anal, intra-anal, peri-anal, transmucosal, transdermal, parenteral, enteral, or local. "Parenteral" refers to a route of administration that is generally associated with injection, including intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the agent or composition may be in the form of solutions or suspensions for infusion or for injection, or as lyophilized powders. Via the enteral route, the agent or composition can be in the form of capsules, gel capsules, tablets, sugar-coated tablets, syrups, suspensions, solutions, powders, granules, emulsions, microspheres or nanospheres or lipid vesicles or polymer vesicles allowing controlled release. Via the topical route, the agent or composition can be in the form of aerosol, lotion, cream, gel, ointment, suspensions, solutions or emulsions. In an embodiment, agent or composition may be provided in a powder form and mixed with a liquid, such as water, to form a beverage. In accordance with the present invention, "administering" can be self-administering. For example, it is considered as "administering" that a subject consumes a composition as disclosed herein.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., ischemia and reperfusion injury) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition.

As used herein, "variants" can include, but are not limited to, those that include conservative amino acid (AA) substitution, SNP variants, degenerate variants, and biologically active portions of a gene. A "degenerate variant" as used herein refers to a variant that has a mutated nucleotide sequence, but still encodes the same polypeptide due to the redundancy of the genetic code. There are 20 naturally occurring amino acids; however some of these share similar characteristics. For example, leucine and isoleucine are bothaliphatic, branched, and hydrophobic. Similarly, aspartic acid and glutamic acid are both small and negatively charged. Conservative substitutions in proteins often have a smaller effect on function than non-conservative mutations. Although there are many ways to classify amino acids, they are often sorted into six main groups on the basis of their structure and the general chemical characteristics of their R groups. A mutation among the same class of amino acids is considered a conservative amino acid substitution.

| Class | Name of the amino acids |
|---|---|
| Aliphatic | Glycine, Alanine, Valine, Leucine, Isoleucine |
| Hydroxyl or Sulfur/Selenium-containing | Serine, Cysteine, Selenocysteine, Threonine, Methionine |
| Cyclic | Proline |
| Aromatic | Phenylalanine, Tyrosine, Tryptophan |
| Basic | Histidine, Lysine, Arginine |
| Acidic and their Amide | Aspartate, Glutamate, Asparagine, Glutamine |

The term "functional" when used in conjunction with "variant" or "fragment" refers to an entity or molecule which possess a biological activity that is substantially similar to a biological activity of the entity or molecule of which it is a variant or fragment thereof. In accordance with the present invention, a GJA1 polypeptide may be modified, for example, to facilitate or improve identification, expression, isolation, storage and/or administration, so long as such modifications do not reduce its function to unacceptable level. In various embodiments, a variant or fragment of the GJA1 polypeptide has at least 10%, 20%, 30%, 40%, 50%, 60%, 70%, 80%, 90%, or 95% of the function of a wild-type GAJ1 isoform (e.g., GJA1-20k and GJA1-11k). As one non-limiting example, a wild-type GAJ1 isoform (e.g., GJA1-20k and GJA1-11k) can have conservative amino acid (AA) substitutions, and these variants often retain a substantial amount of biological activity and can hence be functional variants.

Very few agents exist to protect against metabolic injury. N-acetylcysteine is sometimes used to protect kidneys after injury and beta-blockers are used in the setting of myocardial ischemia. We are the first to discover the beneficial effect of GJA1-20k on mitochondrial health. The metabolism related findings are completely novel.

In the heart, trafficking of connexin 43 (Cx43) to the cell-cell border is a continuous process critical for intercellular coupling and coordination of each heartbeat. We have found that microtubules and key associated proteins deliver Cx43 directly to adherens junctions in a process called Targeted Delivery (see e.g., Shaw et al.; Cell 2007, Smyth et al., JCI 2010; and Shaw, Dev Cell, 2014, which are herein incorporated by reference in their entirety as though fully set forth). We also found that Cx43 mRNA generates smaller isoforms by internal initiation of translation, of which the 20 kDa isoform GJA1-20k is needed for full-length Cx43 localization to cell borders (Smyth and Shaw, Cell Reports 2013, which is herein incorporated by reference in its entirety as though fully set forth).

However, in addition to forming communication channels at the cell surface, Cx43 may have non-canonical roles such as cell survival and ischemic injury protection. We were surprised to discover that GJA1-20k is not only upregulated with ischemic injury but also very strongly localizes to mitochondria, and increases cell survival. We further found GJA1-20k to be enriched at the mitochondrial/microtubule interface, actively loading mitochondria onto microtubules for peripheralization, protecting against organelle fragmentation and cell death upon oxidative stress. The beneficial effects of internally translated GJA1-20k on mitochondrial trafficking and function are exclusive, and do not extend to the full-length Cx43 protein.

Therefore, we identified that a newly described endogenous small isoform of the Cx43 gap junction protein localizes to the mitochondria upon ischemic injury to increase cell survival by facilitating mitochondrial transport along microtubules. Our studies reveal GJA1-20k as a novel and potent regulator of the mitochondria, and introduce it as a therapeutic agent for organs subject to ischemia/reperfusion injury.

In various embodiments, we provide GJA1-20k, an alternatively translated isoform of the Cx43 gene GJA1, as a therapeutic agent for metabolic protection. We demonstrated that GJA1-20k localizes to mitochondria and provides metabolic protection. In various embodiments, this invention provides treatment to tissue damage and cell death resulting from ischemia and reperfusion injury in various organs (e.g., heart, brain and kidney). For example, injectable peptides are provided to limit oxidative and metabolic induced cell death during active or expected ischemic damage. These instances include myocardial infarction, open heart surgery and cardiopulmonary bypass, coronary artery reperfusion, ischemic stroke in brain, and kidney prior to use of nephrotoxic contrast agent for imaging.

In various embodiments, the inventors use GJA1-20k as a therapeutic agent to treat medical conditions related to ischemia/reperfusion. In various embodiments, for efficient delivery, this isoform may be tagged with cell penetrating/internalization peptides (e.g., TAT, poly-arginine, and antennapedia).

Proteins and Expression Vectors

Various embodiments of the present invention provide a composition that comprises a GJA1 polypeptide or a functional variant or fragment thereof. In some embodiments, the variant is a variant with conservative AA substitutions. In some embodiments, a composition as described herein is used as an antigen to generate an antibody specifically binding to a GJA1 polypeptide.

As used herein, the term "GJA1 polypeptide" refers to any polypeptide having an amino acid (AA) sequence translated from the GJA1 gene or a fragment of that AA sequence. The GJA1 gene encodes the full-length Connexin 43 (Cx43) protein (i.e., the longest isoform GJA1-43k) as well as its various shorter isoforms (e.g., GJA1-32k, GJA1-29k, GJA1-26k, GJA1-20k, GJA1-11k, and GJA1-7k). In some embodiments, various GJA1 polypeptides as described herein are used as antigens to generate antibodies specifically binding to them.

As used herein, the term "GJA1-32k polypeptide" refers to any polypeptide having an amino acid (AA) sequence of GJA1-32k. As used herein, the term "GJA1-29k polypeptide" refers to any polypeptide having an amino acid (AA) sequence of GJA1-29k. As used herein, the term "GJA1-26k polypeptide" refers to any polypeptide having an amino acid (AA) sequence of GJA1-26k. As used herein, the term "GJA1-20k polypeptide" refers to any polypeptide having an amino acid (AA) sequence of GJA1-20k. As used herein, the term "GJA1-11k polypeptide" refers to any polypeptide having an amino acid (AA) sequence of GJA1-11k. As used herein, the term "GJA1-7k polypeptide" refers to any polypeptide having an amino acid (AA) sequence of GJA1-7k.

In various embodiments, the GJA1 gene is a gene of mammal. In various embodiments, the GJA1 gene is a gene of primate, for example, human, chimpanzee, gorilla, or monkey. In various embodiments, the GJA1 gene is a gene of horse, goat, donkey, cow, bull, or pig. In various embodiments, the GJA1 gene is a gene of a rodent, for example, mouse, rat, or guinea pig. In various embodiments, the GJA1 gene is a gene of chicken, duck, frog, dog, cat, or rabbit.

While the present invention has described the shorter Cx43 isoforms using examples in the context of the human GJA1 gene (for example, as set forth in the Reference Sequence (REFSEQ) database: accession NM_000165; NP_000156), one of ordinary skill in the art would understand how identify them in any other species, for example, through homology comparison and sequence alignment. As an example illustrating this process, human GJA1-20k has the following sequence (AA is number according to the full-length human Cx43; that is, human GJA1-20k is AA 213-382 of human Cx43—SEQ ID NO:1):

```
Human  213  MLVVSLVSLALNIIELFYVFFKGVKDRVKGKSDPYHATSGALSPAKDCGSQKYAYFNGCS  272
Human  273  SPTAPLSPMSPPGYKLVTGDRNNSSCRNYNKQASEQNWANYSAEQNRMGQAGSTISNSHA  332
Human  333  QPEDFPDDNQNSKKLAAGHELQPLAIVDQRPSSRASSRASSRPRPDDLEI            382
```

One of ordinary skill in the art would understand how to perform homology comparison and sequence alignment (for example, using Basic Local Alignment Search Tool) between this human GJA1-20k (SEQ ID NO:1) and mouse GJA1-20k (SEQ ID NO: 2) (for example, as set forth in Reference Sequence (REFSEQ) database: accession NM_010288; NP_034418) as follows:

```
human  213  MLVVSLVSLALNIIELFYVFFKGVKDRVKGKSDPYHATSGALSPAKDCGSQKYAYFNGCS  272
            MLVVSLVSLAINIIELFYVFFKGVKDRVKG+SDPYHAT+G LSP+KDCGS KYAYFNGCS mouse  213  MLVVSLVSLALNIIELFYVFFKGVKDRVKGRSDPYHATTGPLSPSKDCGSPKYAYFNGCS  272 human  273  SPTAPLSPMSPPGYKLVTGDRNNSSCRNYNKQASEQNWANYSAEQNRMGQAGSTISNSHA  332
            SPTAPLSPMSPPGYKLVTGDRNNSSCRNYNKQASEQNWANYSAEQNRMGQAGSTISNSHA mouse  273  SPTAPLSPMSPPGYKLVTGDRNNSSCRNYNKQASEQNWANYSAEQNRMGQAGSTISNSHA  332 human  333  QPFDFPDDNQNSKKLAAGHELQPLAIVDQRPSSRASSRASSRPRPDDLEI            382
            QPFDFPDD+QN+KK+AAGHELQPLAIVDQRPSSRASSRASSRPRPDDLEI mouse  333  QPFDFPDDSQNAKKVAAGHELQPLAIVDQRPSSRASSRASSRPRPDDLEI            382
```

As such, the mouse GJA1-20k is identified to have the following sequence (AA is number according to the full-length mouse Cx43; that is, mouse GJA1-20k is AA 213-382 of mouse Cx43—SEQ ID NO:2):

```
mouse  213  MLVVSLVSLALNIIELFYVFFKGVKDRVKGRSDPYHATTGPLSPSKDCGSPKYAYFNGCS  272 mouse  273  SPTAPLSPMSPPGYKLVTGDRNNSSCRNYNKQASEQNWANYSAEQNRMGQAGSTISNSHA  332 mouse  333  QPFDFPDDSQNAKKVAAGHELQPLAIVDQRPSSRASSRASSRPRPDDLEI            382
```

Similarly, the rat GJA1-20k is identified to have the following sequence (AA is number according to the full-length rat Cx43; that is, rat GJA1-20k is AA 213-382 of rat Cx43—SEQ ID NO:3):

```
Rat  213  MLVVSLVSLALNIIELFYVFFKGVKDRVKGRSDPYHATTGPLSPSKDCGSPKYAYFNGCS  272

Rat  273  SPTAPLSPMSPPGYKLVTGDRNNSSCRNYNKQASEQNWANYSAEQNRMGQAGSTISNSHA  332

Rat  333  QPFDFPDDNQNAKKVAAGHELQPLAIVDQRPSSRASSRASSRPRPDDLEI            382
```

In various embodiments, the GJA1 polypeptide can be modified for better production, storage, administration and delivery efficiency etc. As one example, the GJA1 polypeptide can be codon optimized for expression in bacteria and/or yeast. As another example, the GJA1 polypeptide can be PEGylated for better stability, better solubility, reduced antigenicity, reduced renal clearance, and prolonged circulatory time. As still another example, the GJA1 polypeptide can be modified with a cell penetrating peptide (CPP).

Cell-penetrating peptides (CPPs) are short peptides that facilitate cellular uptake of various molecular cargo (e.g., polypeptides and proteins). The "cargo" is associated with CPPs either through chemical linkage via covalent bonds or through non-covalent interactions. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. Non-limiting examples of CCPs include trans-activating transcriptional activator (TAT, GRKKRRQRRRPQ—SEQ ID NO: 6), Poly-arginine (RRRRRRRR, D-isomers—SEQ ID NO: 7), Antennapedia (RQIKIWFQNRRMKWKK—SEQ ID NO: 8), Pep-1 (see e.g., Morris et al., Nat Biotechnol. 2001 December; 19(12):1173-6. A peptide carrier for the delivery of biologically active proteins into mammalian cells), MPG (see e.g., Morris et al., Nucleic Acids Res. 1997 Jul. 15; 25(14):2730-6. A new peptide vector for efficient delivery of oligonucleotides into mammalian cells), CADY (see e.g., Crombez et al., Mol Ther. 2009 January; 17(1): 95-103. doi: 10.1038/mt.2008.215. Epub 2008 Oct. 28. A new potent secondary amphipathic cell-penetrating peptide for siRNA delivery into mammalian cells), and TP10 (see e.g., El-Andaloussi et al., J Control Release. 2005 Dec. 10; 110(1):189-201. Epub 2005 Oct. 25. TP10, a delivery vector for decoy oligonucleotides targeting the Myc protein).

In various embodiments, the GJA1 polypeptide is covalently and/or non-covalently conjugated to a CPP.

In various embodiments, the covalent conjugation is a protein fusion in which the CPP and the GJA1 polypeptide are translated together. In some embodiments, the GJA1 polypeptide is fused to a cell penetrating peptide (CPP). In some embodiments, the CPP is fused to the N-terminus and/or C-terminus the GJA1 polypeptide. In some embodiments, the CPP is located inside the GJA1 polypeptide.

In various embodiments, the covalent conjugation is a chemical linkage between the CPP and the GJA1 polypeptide which have been produced separately before the chemical linkage. In some embodiments, the chemical linkage is non-cleavable. In other embodiments, the chemical linkage is cleavable. Non-limiting examples of the chemical linkage includes disulfide, amide, thiazolidine, oxime and hydrazine bonds.

In various embodiments, the non-covalent conjugation involves forming a complex between the CPP and the GJA1 polypeptide through electrostatic and/or hydrophobic interactions.

In various embodiments, the GJA1 polypeptide is GJA1-32k, GJA1-29k, GJA1-26k, GJA1-20k, GJA1-11k, or GJA1-7k, or a functional variant or fragment thereof. In some embodiments, the variant is a variant with conservative AA substitutions. In some embodiments, the GJA1 polypeptide is GJA1-32k, GJA1-29k, GJA1-26k, GJA1-20k, GJA1-11k, or GJA1-7k, or a functional fragment thereof. In some embodiments, the GJA1 polypeptide is used as an antigen to generate an antibody specifically binding to the GJA1 polypeptide.

In various embodiments, the GJA1 polypeptide is GJA1-20k or a functional variant or fragment thereof. In some embodiments, the variant is GJA1-20k with conservative AA substitutions. In some embodiments, the functional variant or fragment of GJA1-20k comprises the AA sequence: KGVKDRVKGKSDPYHATSGALSPAKDC—SEQ ID NO: 4. In some embodiments, the N-terminus or C-terminus of the GJA1-20k or its functional variant or fragment is fused to a CPP. In other embodiments, both the N-terminus and C-terminus of the GJA1-20k or its functional variant or fragment are fused to a CPP. In various embodiments, the GJA1-20k or its functional variant or fragment is covalently conjugated to a CPP through a chemical linkage. In accordance with the present invention, the chemical linkage can be cleavable or non-cleavable. Non-limiting examples of the chemical linkage includes disulfide, amide, thiazolidine, oxime and hydrazine bonds. In various embodiments, the GJA1-20k or its functional variant or fragment is non-covalently conjugated to a CPP through electrostatic and/or hydrophobic interactions; that is, a complex is formed between the GJA1-20k or its functional variant or fragment and the CPP.

In various embodiments, the GJA1 polypeptide is GJA1-32k or a functional variant or fragment thereof. In some embodiments, the variant is GJA1-32k with conservative AA substitutions. In some embodiments, the N-terminus or C-terminus of the GJA1-32k or its functional variant or fragment is fused to a CPP. In other embodiments, both the N-terminus and C-terminus of the GJA1-32k or its functional variant or fragment are fused to a CPP. In various embodiments, the GJA1-32k or its functional variant or fragment is covalently conjugated to a CPP through a chemical linkage. In accordance with the present invention, the chemical linkage can be cleavable or non-cleavable. Non-limiting examples of the chemical linkage includes disulfide, amide, thiazolidine, oxime and hydrazine bonds. In various embodiments, the GJA1-32k or its functional variant or fragment is non-covalently conjugated to a CPP through electrostatic and/or hydrophobic interactions; that is, a complex is formed between the GJA1-32k or its functional variant or fragment and the CPP.

In various embodiments, the GJA1 polypeptide is GJA1-29k or a functional variant or fragment thereof. In some embodiments, the variant is GJA1-29k with conservative AA substitutions. In some embodiments, the N-terminus or C-terminus of the GJA1-29k or its functional variant or fragment is fused to a CPP. In other embodiments, both the N-terminus and C-terminus of the GJA1-29k or its functional variant or fragment are fused to a CPP. In various embodiments, the GJA1-29k or its functional variant or fragment is covalently conjugated to a CPP through a chemical linkage. In accordance with the present invention, the chemical linkage can be cleavable or non-cleavable. Non-limiting examples of the chemical linkage includes disulfide, amide, thiazolidine, oxime and hydrazine bonds. In various embodiments, the GJA1-29k or its functional variant or fragment is non-covalently conjugated to a CPP through electrostatic and/or hydrophobic interactions; that is, a complex is formed between the GJA1-29k or its functional variant or fragment and the CPP.

In various embodiments, the GJA1 polypeptide is GJA1-26k or a functional variant or fragment thereof. In some embodiments, the variant is GJA1-26k with conservative AA substitutions. In some embodiments, the N-terminus or C-terminus of the GJA1-26k or its functional variant or fragment is fused to a CPP. In other embodiments, both the N-terminus and C-terminus of the GJA1-26k or its functional variant or fragment are fused to a CPP. In various embodiments, the GJA1-26k or its functional variant or fragment is covalently conjugated to a CPP through a chemical linkage. In accordance with the present invention, the chemical linkage can be cleavable or non-cleavable. Non-limiting examples of the chemical linkage includes disulfide, amide, thiazolidine, oxime and hydrazine bonds. In various embodiments, the GJA1-26k or its functional variant or fragment is non-covalently conjugated to a CPP through electrostatic and/or hydrophobic interactions; that is, a complex is formed between the GJA1-26k or its functional variant or fragment and the CPP.

In various embodiments, the GJA1 polypeptide is GJA1-11k or a functional variant or fragment thereof. In some embodiments, the variant is GJA1-11k with conservative AA substitutions. In some embodiments, the N-terminus or C-terminus of the GJA1-11k or its functional variant or fragment is fused to a CPP. In other embodiments, both the N-terminus and C-terminus of the GJA1-11k or its functional variant or fragment are fused to a CPP. In various embodiments, the GJA1-11k or its functional variant or fragment is covalently conjugated to a CPP through a chemical linkage. In accordance with the present invention, the chemical linkage can be cleavable or non-cleavable. Non-limiting examples of the chemical linkage includes disulfide, amide, thiazolidine, oxime and hydrazine bonds. In various embodiments, the GJA1-11k or its functional variant or fragment is non-covalently conjugated to a CPP through electrostatic and/or hydrophobic interactions; that is, a complex is formed between the GJA1-11k or its functional variant or fragment and the CPP.

In various embodiments, the GJA1 polypeptide is GJA1-7k or a functional variant or fragment thereof. In some embodiments, the variant is GJA1-7k with conservative AA substitutions. In some embodiments, the N-terminus or C-terminus of the GJA1-7k or its functional variant or fragment is fused to a CPP. In other embodiments, both the N-terminus and C-terminus of the GJA1-7k or its functional variant or fragment are fused to a CPP. In various embodiments, the GJA1-7k or its functional variant or fragment is covalently conjugated to a CPP through a chemical linkage. In accordance with the present invention, the chemical linkage can be cleavable or non-cleavable. Non-limiting examples of the chemical linkage includes disulfide, amide, thiazolidine, oxime and hydrazine bonds. In various embodiments, the GJA1-7k or its functional variant or fragment is non-covalently conjugated to a CPP through electrostatic and/or hydrophobic interactions; that is, a complex is formed between the GJA1-7k or its functional variant or fragment and the CPP.

Various embodiments of the present invention provide a composition that comprises GJA1-32k covalently and/or non-covalently conjugated to a CPP. Various embodiments of the present invention provide a composition that comprises GJA1-32k fused to a CPP. Various embodiments of the present invention provide a composition that comprises GJA1-29k covalently and/or non-covalently conjugated to a CPP. Various embodiments of the present invention provide a composition that comprises GJA1-29k fused to a CPP. Various embodiments of the present invention provide a composition that comprises GJA1-26k covalently and/or non-covalently conjugated to a CPP. Various embodiments of the present invention provide a composition that comprises GJA1-26k fused to a CPP. Various embodiments of the present invention provide a composition that comprises GJA1-20k covalently and/or non-covalently conjugated to a CPP. Various embodiments of the present invention provide a composition that comprises GJA1-20k fused to a CPP. Various embodiments of the present invention provide a composition that comprises GJA1-11k covalently and/or non-covalently conjugated to a CPP. Various embodiments of the present invention provide a composition that comprises GJA1-11k fused to a CPP. Various embodiments of the present invention provide a composition that comprises GJA1-7k covalently and/or non-covalently conjugated to a CPP. Various embodiments of the present invention provide a composition that comprises GJA1-7k fused to a CPP. In some embodiments, a composition as described herein is used as an antigen to generate an antibody specifically binding to a GJA1 polypeptide.

Various embodiments of the present invention provide a method of obtaining a reagent. The method comprises: providing a GJA1 polypeptide or a functional variant or fragment thereof; and conjugating a cell penetrating peptide covalently or non-covalently to the GJA1 polypeptide or the functional variant or fragment thereof, thereby obtaining the conjugate as the reagent. In some embodiments, the variant is a variant with conservative AA substitutions. In some embodiments, the reagent as described herein is used as an antigen to generate an antibody specifically binding to a GJA1 polypeptide.

Various embodiments of the present invention provide a gene expression vector. Various embodiments of the present invention provide a composition that comprises the gene expression vector. The gene expression vector comprises a sequence of a GJA1 polypeptide or a functional variant or fragment thereof, wherein the gene expression vector is configured for expressing the GJA1 polypeptide or the functional variant or fragment thereof. In some embodiments, the variant is a variant with conservative AA substitutions. In various embodiments, the variant can comprise of 1, 2, 3, 4, 5, 6, 7, 8, 9, 10 conservative AA substitutions.

In some embodiments, various gene expression vectors as described herein are used to produce various GJA1 polypeptides or their functional variants. For example, various gene expression vectors are introduced into a bacteria or yeast to produce various GJA1 polypeptides or their functional variants, which are later isolated.

In various embodiments, the gene expression vector is a plasmid. In various embodiments, the gene expression vector is a viral vector, adeno-associated virus (AAV) vector, recombinant AAV (rAAV) vector, single-stranded AAV vector, double-stranded AAV vector, or self-complementary AAV (scAAV) vector, or a combination thereof. In various embodiments, the gene expression vector is a polynucleotide or a virus particle. In various embodiments, the serotype of the virus particle is AAV1, AAV2, AAV3, AAV4, AAV5, AAV6, AAV7, AAV8, AAV9, AAV10, AAV11, or AAV12, or a hybrid serotype thereof.

Treatment Methods

As described in various embodiments herein, the present invention provides a GJA1-20k polypeptide, its functional variants, and gene expression vectors configured for expressing the GJA1-20k polypeptide or its functional variants. In some embodiments, these polypeptides and gene expression vectors can be used as therapeutic agents for treating various conditions. For example, the GJA1-20k polypeptide, its functional variants, and gene expression vectors configured for expressing the GJA1-20k polypeptide or its functional variants are provided as a pharmaceutical composition. In various embodiments, the GJA1-20k polypeptide and its functional variants can be administered as a therapeutic agent (e.g., protein therapy) to a subject to provide metabolic protection. In various embodiments, the gene expression vector of the GJA1-20k polypeptide and its functional variants can be administered as a therapeutic agent (e.g., gene therapy) to a subject to provide metabolic protection. Various embodiments of the present invention provide a method of treating, preventing, reducing the likelihood of having, reducing the severity of and/or slowing the progression of a condition in a subject. The method comprises: providing a GJA1-20k polypeptide or a functional variant or fragment thereof as described herein; and administering a therapeutically effective amount of the GJA1-20k polypeptide or the functional variant or fragment thereof to the subject, thereby treating, preventing, reducing the likelihood of having, reducing the severity of and/or slowing the progression of the condition in the subject. In some embodiments, the variant is a variant with conservative AA substitutions.

Various embodiments of the present invention provide a method of treating, preventing, reducing the likelihood of having, reducing the severity of and/or slowing the progression of a condition in a subject. The method comprises providing a gene expression vector comprising a sequence of a GJA1-20k polypeptide or a functional variant or fragment thereof, wherein the gene expression vector is configured for expressing the GJA1-20k polypeptide or the functional variant or fragment thereof; and administering a therapeutically effective amount of the gene expression vector to the subject, thereby treating, preventing, reducing the likelihood of having, reducing the severity of and/or slowing the progression of the condition in the subject. In some embodiments, the variant is a variant with conservative AA substitutions. In various embodiments, the variant can comprise of 1, 2, 3, 4, 5, 6, 7, 8, 9, 10 conservative AA substitutions.

In various embodiments, the condition is metabolic stress, ischemia, reperfusion injury, myocardial infarction, open heart surgery, cardiopulmonary bypass, coronary artery reperfusion, stroke, ischemic stroke, or nephrotoxicity, or a combination thereof.

In various embodiments, the subject is a human. In various embodiments, the subject is a mammalian subject including but not limited to human, monkey, ape, dog, cat, cow, horse, goat, pig, rabbit, mouse and rat.

Various embodiments of the present invention provide a method of protecting a cell from metabolic stress. The method comprises: providing a GJA1-20k polypeptide or a functional variant or fragment thereof as described herein; and contacting the cell with the GJA1-20k polypeptide or the functional variant or fragment thereof, thereby protecting the cell from metabolic stress. In some embodiments, the variant is a variant with conservative AA substitutions.

Various embodiments of the present invention provide a method of protecting a cell from metabolic stress. The method comprises: providing a gene expression vector comprising a sequence of a GJA1-20k polypeptide or a functional variant or fragment thereof, wherein the gene expression vector is configured for expressing the GJA1-20k polypeptide or the functional variant or fragment thereof; and contacting the cell with gene expression vector, thereby protecting the cell from metabolic stress. In accordance with the present invention, the gene expression vector expresses the GJA1-20k polypeptide or the functional variant or fragment thereof in the cell. In some embodiments, the variant is a variant with conservative AA substitutions.

In various embodiments, the metabolic stress is induced by ischemia, reperfusion injury, myocardial infarction, open heart surgery, cardiopulmonary bypass, coronary artery reperfusion, stroke, ischemic stroke, or nephrotoxicity, or a combination thereof.

In various embodiments, the administration of the GJA1-20k polypeptide or a functional variant or fragment thereof results in a cardioprotective effect. In various embodiments, the cardioprotective effect comprises a reduction in basal mitochondrial dependent oxygen consumption and maximal respiratory capacity.

In various embodiments, the present invention provides for a method of treating, preventing, reducing the likelihood of having, reducing the severity of and/or slowing the progression of a condition in a subject who has had a previous myocardial infarction, comprising providing a GJA1-20k polypeptide or a functional variant or fragment thereof; and administering a therapeutically effective amount of the GJA1-20k polypeptide or the functional variant or fragment thereof to the subject, thereby treating, preventing, reducing the likelihood of having, reducing the severity of and/or slowing the progression of the condition in the subject. In various embodiments, the subject is a person who has had a previous myocardial infarction. In other embodiments, the subject is a person who is at risk for a myocardial infarction.

In some embodiments, the GJA1-20k polypeptide or a functional variant or fragment thereof is administered using gene transfer. In various other embodiments, the GJA1-20k polypeptide or a functional variant or fragment thereof is administered using the AAV9 vector.

In various embodiments, the GJA1-20k polypeptide or a functional variant or fragment thereof is administered to the subject to treat a first or second instance of ischemic insult. In some embodiments, the GJA1-20k polypeptide or a functional variant or fragment thereof is administered before the ischemic insult. In other embodiments, the GJA1-20k polypeptide or a functional variant or fragment thereof is administered after an ischemic insult. In various embodiments, the GJA1-20k polypeptide or a functional variant or fragment thereof is protective of a subsequent instance of ischemic insult. In various embodiments, the GJA1-20k polypeptide or a functional variant or fragment thereof is protective of a subsequent myocardial infarction. In various embodiments, myocardial infarct size is reduced. In various other embodiments, the myocardial infarct size is reduced by 20%, 30%, 40% or 50% compared to a reference value. In various other embodiments, administration of the GJA1-20k polypeptide or a functional variant or fragment thereof limits the damage induced by acute ischemia and infarction.

In various embodiments, a therapeutic agent as described herein (e.g., GJA1-20k polypeptide, its functional variants, and gene expression vectors configured for expressing the GJA1-20k polypeptides or its functional variants) may be administered once a day (SID/QD), twice a day (BID), three times a day (TID), four times a day (QID), or more, so as to administer an effective amount of the therapeutic agent to the subject, where the effective amount is any one or more of the doses described herein. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

In various embodiments, a therapeutic agent as described herein is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In various embodiments, a therapeutic agent as described herein is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$, or a combination thereof. In various embodiments, a therapeutic agent as described herein is administered once, twice, three or more times. In some embodiments, a therapeutic agent as described herein is administered 1-3 times per day, 1-7 times per week, 1-9 times per month, or 1-12 times per year. Still in some embodiments, a therapeutic agent as described herein is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. Here, "mg/kg" refers to mg per kg body weight of the subject, and "mg/m$^2$" refers to mg per m$^2$ body surface area of the subject. In certain embodiments, a therapeutic agent as described herein is administered to a human.

In various embodiments, the effective amount of a therapeutic agent as described herein is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg/day, or a combination thereof. In various embodiments, the effective amount of a therapeutic agent as described herein is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/m$^2$/day, or a combination thereof. In various embodiments, the effective amount of a therapeutic agent as described herein is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg/day, or a combination thereof. In various embodiments, the effective amount of a therapeutic agent as described herein is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$/day, or a combination thereof. Here, "µg/kg/day" or "mg/kg/day" refers to µg or mg per kg body weight of the subject per day, and "µg/m$^2$/day" or "mg/m$^2$/day" refers to µg or mg per m$^2$ body surface area of the subject per day.

In some embodiments, a therapeutic agent as described herein may be administered at the prevention stage of a condition (i.e., when the subject has not developed the condition but is likely to or in the process to develop the condition). In other embodiments, a therapeutic agent as described herein may be administered at the treatment stage of a condition (i.e., when the subject has already developed the condition). Still in other embodiments, a therapeutic agent as described herein may be administered at the maintenance stage after treating a condition (i.e., when the subject has already been treated but is still under care for suppressing recurrence). As a non-limiting example, the target condition is ischemia. In this exemplar situation, the patient may be treated with the methods described herein when the patient has not yet developed ischemia, or is likely to develop ischemia, or is in the process of developing ischemia, or has already developed ischemia, or has been treated for ischemia (for example, through a surgery).

In various embodiments, the GJA1-20k polypeptide or a functional variant or fragment thereof is administered to the subject to treat a first or second instance of ischemic insult. In some embodiments, the GJA1-20k polypeptide or a functional variant or fragment thereof is administered before the ischemic insult. In other embodiments, the GJA1-20k polypeptide or a functional variant or fragment thereof is administered after an ischemic insult. In various embodiments, the GJA1-20k polypeptide or a functional variant or fragment thereof is protective of a subsequent instance of ischemic insult. In various embodiments, the GJA1-20k polypeptide or a functional variant or fragment thereof is protective of a subsequent myocardial infarction.

In accordance with the invention, a therapeutic agent as described herein may be administered using the appropriate modes of administration. In accordance with the invention, various routes may be utilized to administer a therapeutic agent as described herein for the claimed methods, including but not limited to intravascular, intravenous, intraarterial, intramuscular, subcutaneous, intraperitoneal, aerosol, nasal, via inhalation, oral, transmucosal, transdermal, parenteral, implantable pump or reservoir, continuous infusion, enteral application, topical application, local application, capsules and/or injections. In various embodiments, a therapeutic agent as described herein is administered intracranially, intraventricularly, intrathecally, epidurally, intradurally, topically, intravascularly, intravenously, intraarterially, intramuscularly, subcutaneously, intraperitoneally, intranasally, or orally.

Many variations and alternative elements have been disclosed in embodiments of the present invention. Still further variations and alternate elements will be apparent to one of skill in the art. Among these variations, without limitation, are the selection of constituent modules for the inventive methods, compositions, kits, and systems, and the various conditions, diseases, and disorders that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. For example, one may consider "5% more or less" to be within the meaning of "about". In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1 GJA1-20k Facilitates Mitochondrial Trafficking on Microtubules for Cell Survival The connexin 43 (Cx43) gap junction protein forms intercellular communication channels, yet also has a critical role in cell survival during ischemic tissue injury. The mechanism of ischemic protection by Cx43 is not understood. The recently discovered GJA1-20k isoform, generated by alternative translation, aids in Cx43 trafficking and increases with metabolic stress and hypoxia. Here we show that while both GJA1-20k and full-length Cx43 are upregulated in cardiac ischemia/reperfusion injury, only GJA1-20k increases cell survival. We find that GJA1-20k strongly localizes to the mitochondria, and the mitochondrial/microtubule interface, effectively loading mitochondria onto microtubules for transport. The presence of GJA1-20k peripheralizes mitochondria and limits organelle fragmentation upon oxidative stress. Mitochondrial enrichment and an intact microtubule binding domain are essential for the ability of GJA1-20k to improve cell survival. Thus, GJA1-20k plays an active protective role in microtubule-based mitochondrial trafficking, introducing it as a potent therapeutic to limit ischemic injury.

GJA1-20k Increases During Oxidative Stress to Coordinate Microtubule-Based Mitochondria Trafficking and Cell Survival In Langendorff-perfused mouse hearts, I/R doubles both Cx43 and GJA1-20k protein levels (FIGS. 1A and 1B). Confocal immunofluorescence of left ventricular tissue indicates that I/R induces both intracellular and lateral localization of Cx43 (FIG. 1C). Biochemical fractionation was used to further differentiate intracellular distribution of Cx43 isoforms. While cytoplasmic, membrane, and mitochondrial Cx43 pools are increased after I/R injury, GJA1-20k is surprisingly increased primarily in membrane- and mitochondria-rich fractions (FIG. 1D). To address whether GJA1-20k localizes to cardiac mitochondria, we transduced adult ventricular myocytes with adenovirus expressing V5 tagged GJA1-43k (lacking all internal methionines to encode only the full-length protein), GJA1-20k, or LacZ. Superresolution STORM imaging of isolated mitochondria (FIG. 1E) confirms the presence of both GJA1-43k and GJA1-20k, with GJA1-20k appearing more uniformly distributed.

Figure 1G:
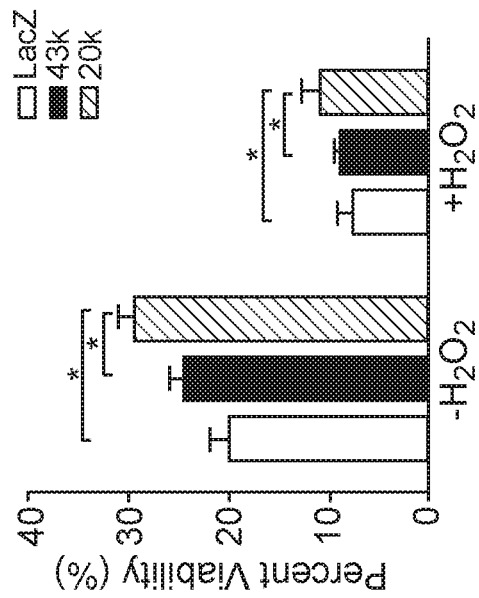
Figure 1H:
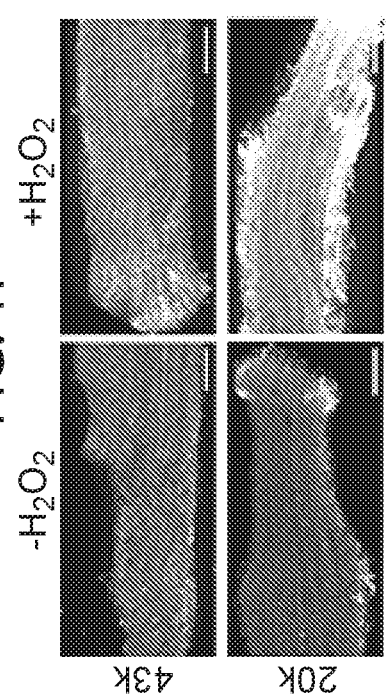
Figure 1I:
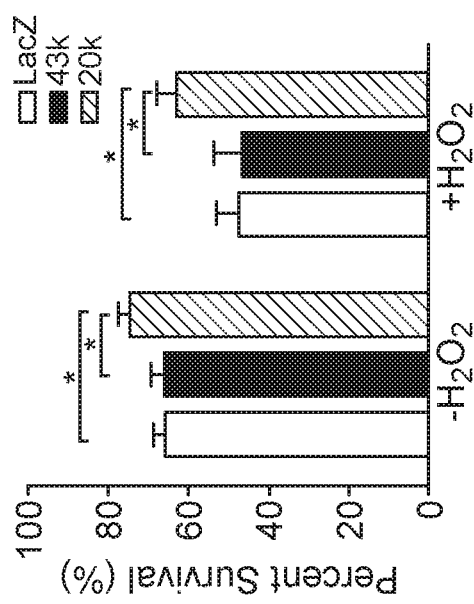

We then asked whether I/R-induced mitochondria-localized GJA1-43k and GJA1-20k affect mitochondrial and cell health. Adult cardiomyocytes transduced with GJA1-43k, GJA1-20k or LacZ virus were subjected to $H_2O_2$-induced oxidative stress, and labeled with mitotracker to identify healthy mitochondria with intact membrane potential. In the presence of $H_2O_2$, GJA1-20k, but not GJA1-43k, resulted in increased lateral mitotracker incorporation (FIGS. 1F and 1G). Subsarcolemmal mitochondria at the cardiomyocyte periphery are a part of the frontline gatekeepers of cellular homeostasis and metabolism, requiring Cx43 for their cardioprotective role. The enhanced peripheral mitochondrial signal in GJA1-20k expressing cells suggests that this isoform may protect against oxidative stress. Using the trypan blue exclusion assay we found that GJA1-20k overexpression increased cardiomyocyte survival by 8.7% and 15.5% before and after $H_2O_2$ induced stress, respectively, as compared to LacZ (FIG. 1H). GJA1-20k also increased cell viability, as revealed by the number of rod-shaped cardiomyocytes, by 9.5% and 3.2% before and after $H_2O_2$, respectively (FIG. 1I).

Figure 2A:
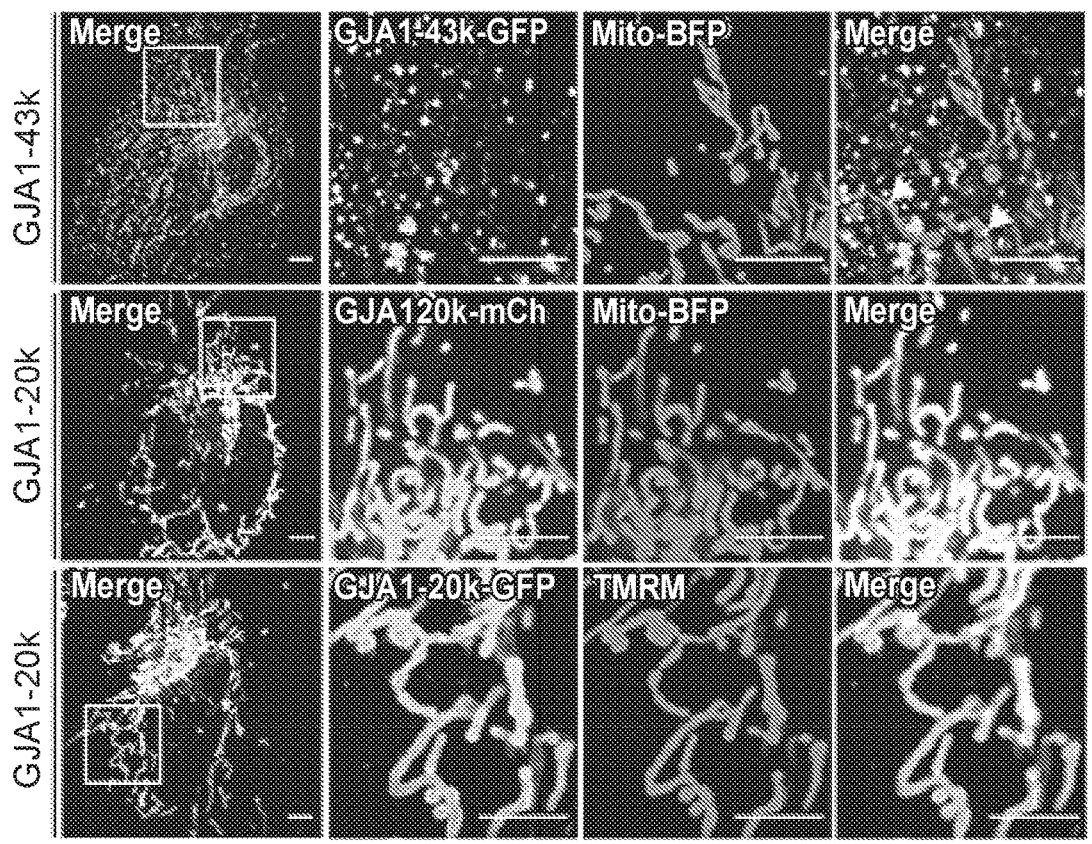
FIGS. 2A-2B depict, in accordance with various embodiments of the invention, GJA1-20k, but not full-length GJA1-43k, delineates the mitochondria network.
Figure 2B:
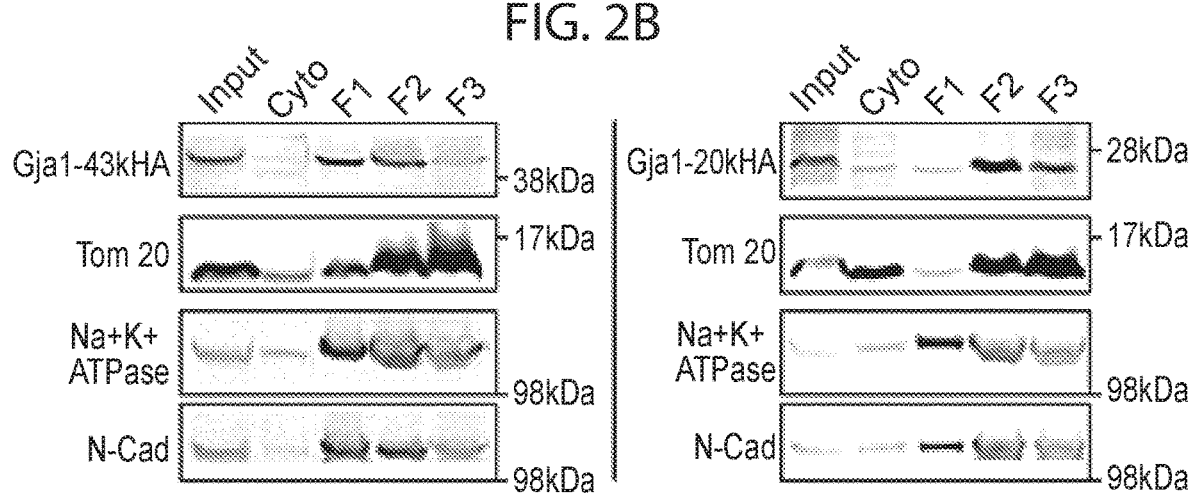

The results of FIGS. 1A-1I indicate that GJA1-20k is enriched in adult cardiomyocyte mitochondria, increases peripheral mitotracker signal upon oxidative stress, and improves cell survival. We then used HeLa cells, which are readily amendable to live-cell microscopy, to address in detail the relationship between GJA1 isoforms and mitochondria (FIG. 2A). While some GJA1-43k puncta colocalize with the mitochondrial marker mito-BFP (arrows), GJA1-20k is expressed throughout actively respiring mitochondria, marked by mito-BFP and the membrane potential indicator tetramethylrhodamine methyl ester (TMRM). GJA1-20k localization is indistinguishable from that of the mitochondrial markers. Ultracentrifugation purification revealed a progressive increase in GJA1-20k but not GJA1-43k in the mitochondria-enriched F3 fraction versus the plasma membrane-enriched F2 and F1 fractions (FIG. 2B). Thus, GJA1-20k preferentially localizes to, and even identifies, all metabolically active mitochondria.

Figure 3A:
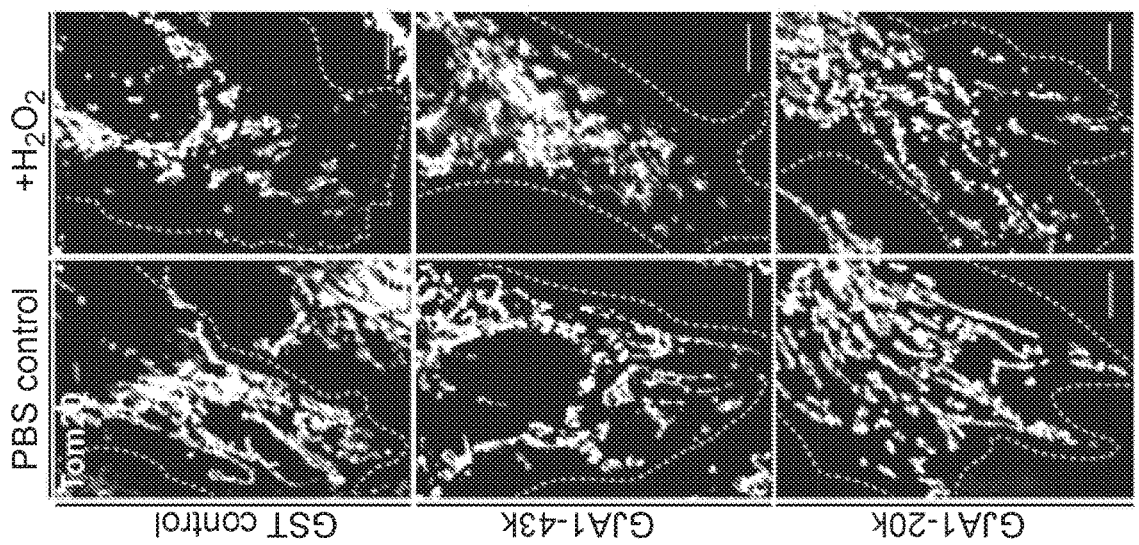
FIGS. 3A-3D depict, in accordance with various embodiments of the invention, GJA1-20k maintains peripheral mitochondria, limiting fragmentation upon oxidative stress.
Figure 3B:
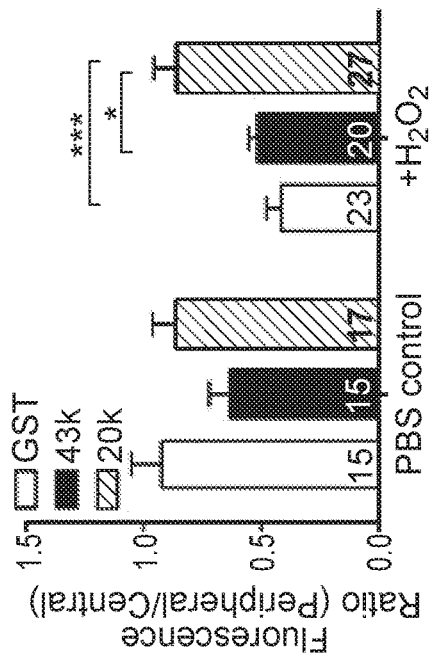
Figure 3C:
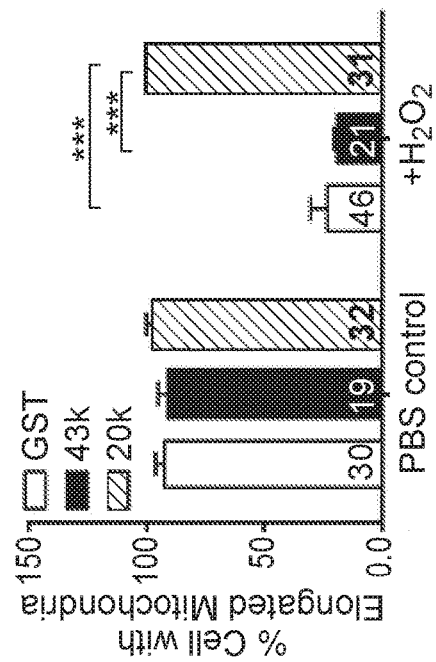

Regulators of mitochondrial morphology and dynamics are becoming increasingly recognized as having a central role in cardioprotection. To address the mechanism of mitochondria-associated rescue of cellular stress by GJA1-20k, we examined mitochondrial localization and morphology in HeLa cells subjected to $H_2O_2$. Mitochondria were identified by anti-Tom20 labeling in cells expressing GFP-tagged GST, GJA1-43k, or GJA1-20k. By confocal fluorescence imaging, an extended reticular mitochondria network is visualized in all cells without $H_2O_2$ (FIG. 3A). Upon $H_2O_2$ treatment, the mitochondria became centralized and fragmented in cells expressing GST and GJA1-43k, but the majority of GJA1-20k cells retained mitochondrial morphology and distribution. Peripheral versus central Tom20 fluorescence and the percentage of cells with elongated mitochondria were quantified. No significant difference was detected between conditions in PBS treated cells, but with $H_2O_2$, only cells expressing GJA1-20k maintained peripheral mitochondria with preserved elongated morphology (FIGS. 3B and 3C).

Figure 3D:
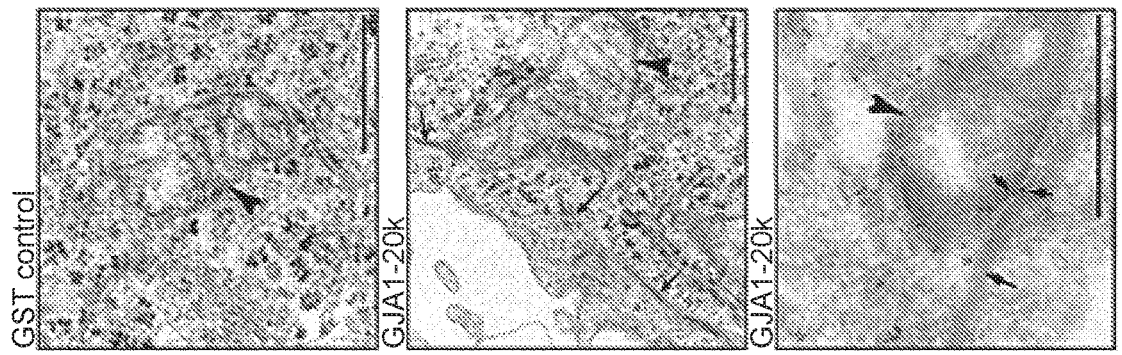

Mitochondrial dynamics and subcellular distribution require ongoing microtubule-based movement. Thus, we examined the spatial relationship of individual mitochondrion and nearby microtubules using transmission electron microscopy (TEM) in transfected HeLa cells. Mitochondria in GJA1-20k-expressing cells appear larger and more closely associated with cytoskeletal fibers in comparison to GST-expressing cells. As seen in FIG. 3D, GJA1-20k expression causes mitochondria to be stretched along microtubules, apparently in the process of transport. We did not find a similar association between mitochondria and microtubules in GST cells. Immunogold labeling further revealed that GJA1-20k localizes to both mitochondria and microtubules, appearing in close apposition at the interface between these structures (FIG. 3D, yellow arrows).

Figure 4A:
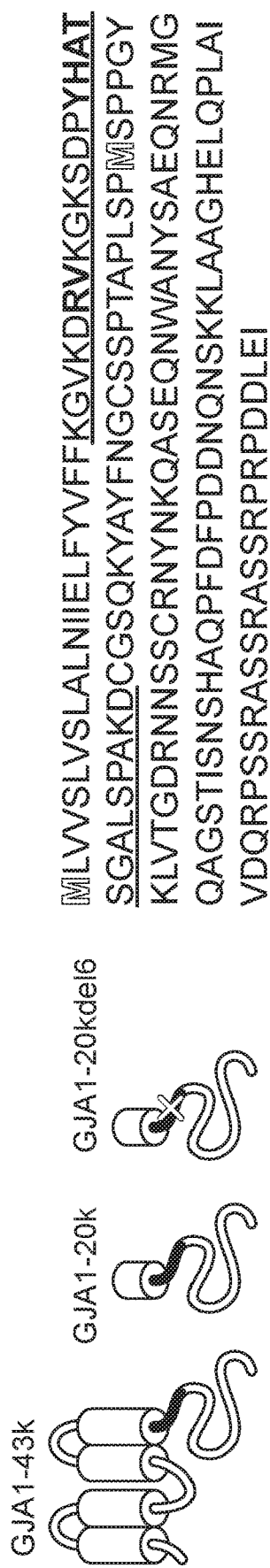
FIGS. 4A-4H depict, in accordance with various embodiments of the invention, GJA1-20k mediates mitochondria trafficking through key microtubule-interacting residues for cellular protection.
Figure 4B:
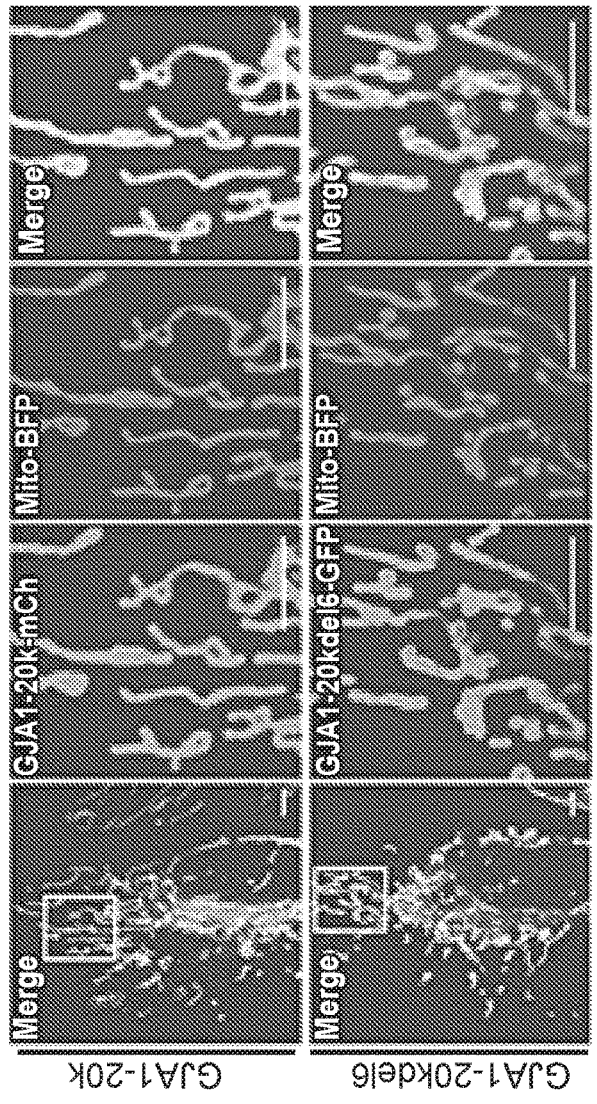
Figure 4C:
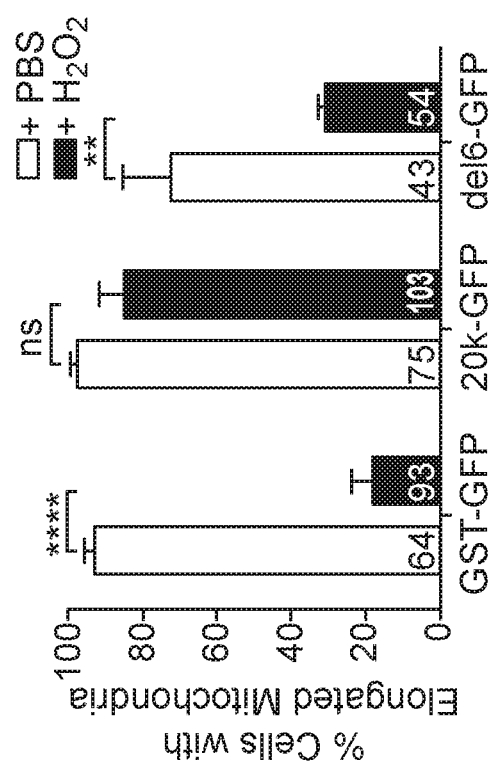
Figure 4D:
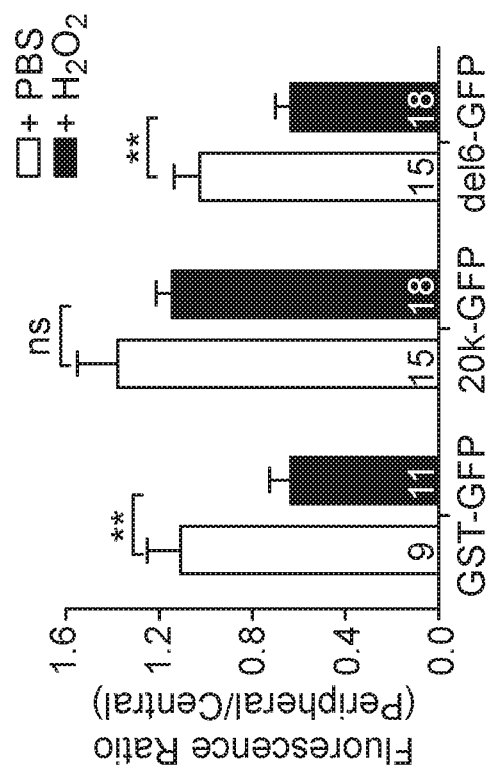

GJA1-20k is required for Cx43 trafficking to the cell-cell border, which suggests a role for this isoform in microtubule-based transport. Based on the strong association between mitochondria and microtubules (FIG. 3D), we tested whether GJA1-20k mediates mitochondrial trafficking along microtubules. The microtubule binding domain of Cx43 has been experimentally defined, and includes amino acids 234-259 (FIG. 4A, underlined) which are free in solution but form three helices when bound to tubulin, as revealed by nuclear magnetic resonance. Within this region, six specific residues were modeled to participate in intermolecular hydrogen bonds with tubulin (red amino acids). We generated a GJA1-20k mutant lacking these key residues (GJA1-20k-del6), which retains its mitochondrial localization (FIG. 4B). Upon $H_2O_2$ treatment, peripheral versus central mitochondrial fluorescence ratio, and the percentage of cells with elongated mitochondria were quantified. Unlike GJA1-20k, the microtubule-binding domain mutant GJA1-20k-del6 failed to provide rescue of mitochondrial localization and morphology in response to oxidative stress (FIGS. 4C and 4D).

Figure 4E:
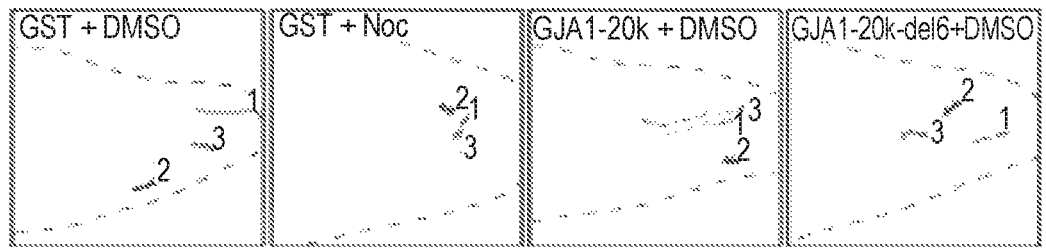
Figure 4F:
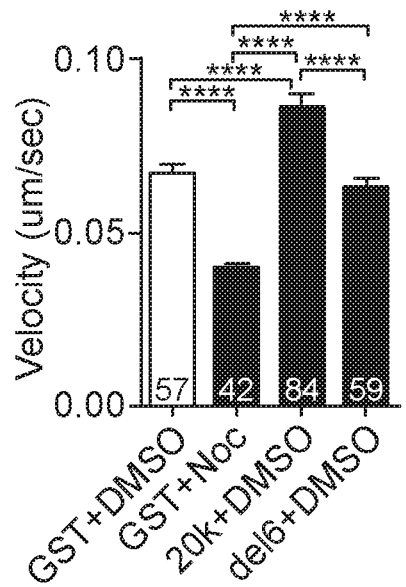
Figure 4G:
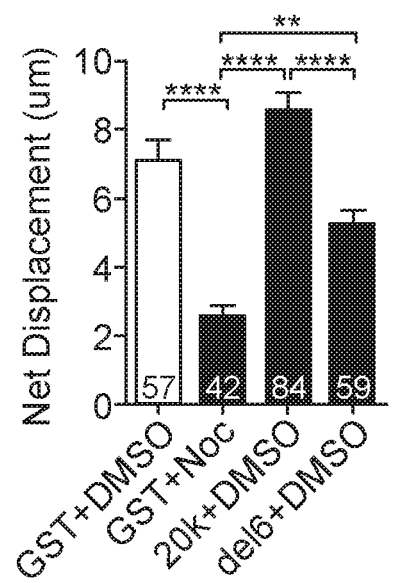

We then examined live-cell mitochondrial dynamics in cells expressing GST, GST treated with nocodazole to disrupt microtubules, GJA1-20k, or GJA1-20k-del6. Mitochondrial dynamics were assessed by tracking individual organelle every 5 seconds over a five-minute period. Typical mitochondrial tracks for each condition are represented in FIG. 4E. Tracking analysis revealed that nocodazole reduced mitochondrial speed and net displacement, the difference of which is microtubule-dependent (FIGS. 4F and 4G). In contrast, GJA1-20k increased mitochondrial speed and displacement, whereas GJA1-20k-del6 cells had the same mean velocity and slightly less net displacement when compared to control cells.

Figure 4H:
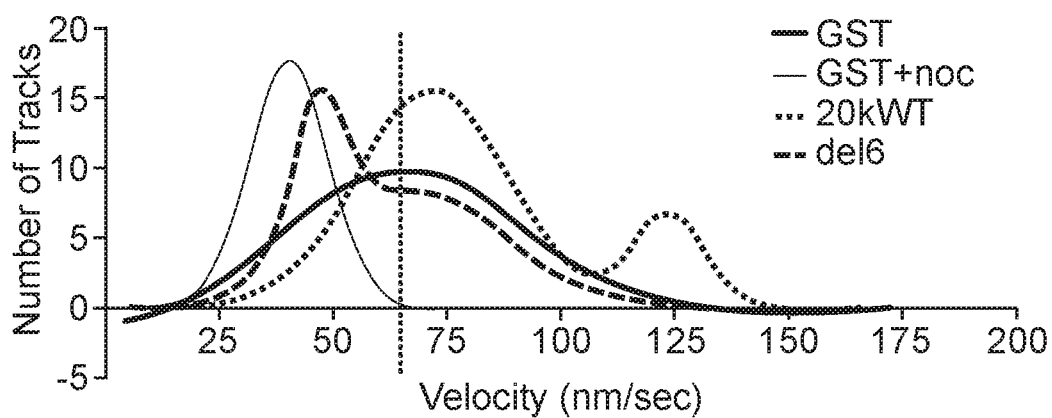

Frequency distribution analyses of the mitochondrial mean velocity for each condition were best fitted with either single or double Gaussian curves (FIG. 4H). The primary peaks of the GST (black), GJA1-20k (blue), and GJA1-20k-del6 (red) curves were similar at ~65 nm/s. Nocodazole shifted the entire GST curve to the left (grey) indicating a loss of fast mitochondrial movement, whereas a secondary curve to the right (more frequently moving at higher speeds) occurred with GJA1-20k cells (blue). In contrast, the secondary peak of GJA1-20k-del6 cells was shifted to the left (lower speeds, red), closer to the nocodazole curve. These data indicate that at baseline, mitochondrial transport occurs at the median speed of 65 nm/sec, but in cells that contain GJA1-20k with an intact microtubule-binding domain, mitochondria occasionally travel at twice the median speed, consistent with kinesin-based transport. Thus, exogenous GJA1-20k increases the chances that mitochondria can utilize microtubule-based transport. These occasional bursts of rapid movement support the role for GJA1-20k in localizing mitochondria to the cell periphery.

Among the non-canonical functions of Cx43 is the ability to provide ischemic preconditioning by which a brief period of ischemia protects against subsequent longer ischemic episodes in the heart and the brain. Mitochondrial localization of Cx43 is believed to help mediate this cardioprotective effect. Our data are supportive of Cx43 mediating ischemic protection, but suggests that a smaller protein product of the GJA1 mRNA, the GJA1-20k isoform, exerts a dominant protective effect on cell survival rather than the full-length protein. Mitochondrial dynamics, which require intimately linked processes of fission/fusion and microtubule-based motor/adaptor transport, are crucial for organelle content exchange and maintenance of a healthy mitochondrial population. The mechanism of cellular protection in our study is based on stress-induced GJA1-20k facilitating mitochondrial loading and progressive movement along the microtubule-mitochondrial interface where GJA1-20k is enriched. Thus, we have identified that GJA1-20k not only mediates full-length Cx43 trafficking, but also is responsible for regulating mitochondrial transport. Mitochondrial regulation by GJA1-20k, a protein that was only recently recognized to exist, provides an important link between cell-cell coupling proteins and the metabolic health of cells. As GJA1-20k, unlike full-length Cx43, is not known to hexamerize or contain complete transmembrane domains, it could serve as a therapeutic by which its introduction, or upregulation by rapamycin treatment, protects ischemic tissues.

GJA1 has one coding exon and therefore cannot provide protein diversity by means of exonal alternative splicing. However, by alternative translation, smaller peptides are generated by the same mRNA, yet without many of the size, hydrophobicity, and regulatory constraints of the larger primary Cx43 protein. It follows then that GJA1-20k can perform novel functions, such as regulation of mitochondrial trafficking, that are distinct from its full-length counterpart.

In vivo mouse experiments with GJA1-20k have shown positive results in terms of cardio protection and trafficking. We injected GJA1-20k into mice with an AAV9 virus vector that has tropism to the heart and then, 3 weeks later, subjected the mice to coronary ligation, which serves as an equivalent of an acute heart attack. GJA1-20k was found to be protective. The controls were GFP and M6L (full length Cx43 without the smaller isoforms). Also, in those injected mice without the coronary ligation, GJA1-20k improved Cx43 gap junction communication in heart cells better than M6L (full length Cx43 without the smaller isoforms) or negative controls. M6L is the full-length wild type Cx43 but its internal translation sites are mutated to limit production of the smaller isoforms.

Langendorff-Perfused Mouse Heart Preparation

C57BL/6 mice used for heart preparations were maintained under sterile barrier conditions. All procedures were reviewed and approved by Cedars-Sinai Medical Center Institutional Animal Care and Use Committee. Langendorff-perfused mouse hearts were subjected to ischemia reperfusion injury as previously described (see e.g., J. W. Smyth et al., Limited forward trafficking of connexin 43 reduces cell-cell coupling in stressed human and mouse myocardium. The Journal of clinical investigation 120, 266 (January, 2010)). Briefly, adult male (12-14 weeks) hearts were dissected in ice-cold modified pH 7.4 Krebs-Henseleit (K-H) solution containing (mM): 118 NaCl, 4.7 KCl, 2.5 $CaCl_2.H_2O$, 1.2 $MgCl_2$, 24 $NaHCO_3$, 1.2 $KH_2PO_4$, 11 glucose, and 0.5 EDTA. The hearts were attached to a Langendorff apparatus (ADInstruments) and retrogradely perfused at a constant rate of 2.5 ml/min with the K-H buffer, which was constantly gassed with 95% $O_2$/5% $CO_2$, and maintained at 37° C. Hearts were allowed to equilibrate for 20 minutes to achieve a steady state before they were subjected to 30 minutes of global ischemia, followed by 60 minutes of reperfusion. Control hearts were perfused continuously throughout the protocol. Immediately after the Langendorff procedure, hearts were homogenized and snap frozen for biochemical studies, or embedded in OCT media (Sakura Finotek) for cryosectioning.

Western Blotting

Hearts were homogenized in radioimmunoprecipitation assay buffer (RIPA) containing (mM): 50 Tris, 150 NaCl, 1 EDTA, 1% TritonX-100, 1% sodium deoxycholate, 1 NaF, 0.2 $Na_3VO_4$, and 1× Halt Protease and Phosphatase Inhibitor Cocktail (Thermo Fisher Scientific). Protein concentration determination (Bio-Rad DC Protein Assay) and western blotting were performed as previously described (see e.g., J. W. Smyth et al., Limited forward trafficking of connexin 43 reduces cell-cell coupling in stressed human and mouse myocardium. The Journal of clinical investigation 120, 266 (January, 2010)). Primary antibodies used include: rabbit anti-Actin N-terminal (1:3000, Sigma-Aldrich), rabbit anti-$CaV_{1.2}$ (1:500, Alomone Labs), and mouse anti-Cx43 CT1 (1:1000, Fred Hutchinson Cancer Center), mouse anti-N-cadherin (1:1000, BD Biosciences), mouse anti-$Na^+/K^+$ ATPase (1:1000, EMD Millipore), rabbit anti-Tom20 (1:1000, Santa Cruz Biotechnology), and mouse anti-HA (1:1000, Sigma-Aldrich). Membranes were imaged using the ChemiDoc MP detection system (Bio-Rad).

Tissue Immunofluorescence

Cryosectioning and tissue immunofluorescence was performed as previously described (see e.g., J. W. Smyth et al., Actin cytoskeleton rest stops regulate anterograde traffic of connexin 43 vesicles to the plasma membrane. Circulation research 110, 978 (Mar. 30, 2012)). Briefly, cryosections (10 μm) were fixed in 2% paraformaldehyde (PFA, Electron Microscopy Services) for 15 minutes at room temperature (RT), blocked and permeabilized at RT for 1 hour with 10% normal goat serum (NGS) and 0.5% TritonX-100 in phosphate-buffered saline (PBS). Primary antibodies were incubated at 4° C. overnight: rabbit anti-Cx43 (1:500; Sigma-Aldrich) and mouse anti-N-cadherin (1:500, BD Biosciences). Secondary detection was carried out using Alexa Fluors (1:500, Thermo Fisher Scientific) before slides were mounted with ProLong Gold Antifade reagent containing DAPI (Thermo Fisher Scientific).

Mitochondrial Fractionation

Mitochondria fractionation of hearts, and HeLa cells transfected with HA-tagged GJA1-43k or GJA1-20k, was performed as previously described (H. Singh et al., Visualization and quantification of cardiac mitochondrial protein clusters with STED microscopy. Mitochondrion 12, 230 (March, 2012)). Briefly, mouse tissue or cells were manually homogenized in isolation buffer A with BSA (mM): 230 mannitol, 70 sucrose, 10 HEPES, 2 EDTA pH 7.2 with KOH, and 1 mg/mL fatty acid free BSA using a Potter Elvehjem homogenizer (Sigma-Aldrich). Homogenates were centrifuged at 1,300×g for 3 min at 4° C. The resulting supernatants were collected and centrifuged at 10,000×g for 10 min at 4° C. Pellets containing crude mitochondria were then overlaid on 30% (v/v) Percoll (Sigma-Aldrich) in buffer B (mM): 250 sucrose, 10 HEPES-Na, 1 EDTA-$Na_2$, pH 7.4. Samples were centrifuged (Optima MAX-XP, Beckman Coulter) in a fixed angle rotor at 50,000×g at 4° C. for 45 min. After ultracentrifugation, three bands were collected and labeled as M1, M2 and M3 from tissues, and three fractions were collected and labeled as F1, F2 and F3 for cells. Each fraction was collected at 12,000×g at 4° C. for 5 min for biochemical analysis.

Cardiomyocyte Transduction, $H_2O_2$ Treatment, and Mitotracker Labeling

Adult mouse ventricular cardiomyocytes were isolated from 12 to 14 week old C57BL/6 mice as previously described (see e.g., D. Gao et al., Dynasore protects mitochondria and improves cardiac lusitropy in Langendorff perfused mouse heart. PloS one 8, e60967 (2013)). After 2 hours of plating, cardiomyocytes were transduced with adenoviruses encoding V5-tagged LacZ, GJA1-20k, or GJA1-43k at 40 M.O.I. overnight in a humidified atmosphere of 5% $CO_2$ at 37° C. Adenoviruses were generated at the University of California Los Angeles CURE Vector Core Facility. The day after transduction, cardiomyocytes were treated with 30 μM $H_2O_2$ (Sigma-Aldrich) for 35 minutes at 37° C. in a humidified atmosphere of 5% $CO_2$. Cells were then treated with 200 nM mitotracker (CMXRos-Red, Thermo Fisher Scientific) in Hanks Balanced Salt Solution (HBSS, Thermo Fisher Scientific) containing 1.2 mM $CaCl_2$ for 20 minutes at 37° C. in a humidified atmosphere of 5% $CO_2$. Cells were fixed with ice-cold methanol for 5 minutes at −20° C., mounted using ProLong Gold Antifade reagent containing DAPI (Thermo Fisher Scientific) and imaged using a Nikon Eclipse Ti confocal microscope with a ×100/1.49 Apo TIRF objective. Mitotracker signal intensity at the cardiomyocyte periphery was analyzed with ImageJ (NIH). First, background was subtracted from each image before fluorescence signal and area values were obtained for the entire cell. Signal and area values were also determined for the inner cytoplasmic region, defined by shrinking the total cell area by 60%. Peripheral mitotracker intensity is calculated by subtracting the inner cytoplasmic intensity (signal× area) from total cellular intensity, and dividing the resulting value by the area difference between whole cell and the inner cytoplasm.

Cardiomyocyte Survival and Viability Assay

Survival and viability assay was performed as previously described (see e.g., D. Gao et al., Dynasore protects mitochondria and improves cardiac lusitropy in Langendorff perfused mouse heart. PloS one 8, e60967 (2013)). Briefly, cardiomyocytes were treated with 30 μM $H_2O_2$ (Sigma-Aldrich) for 35 min at 37° C. in a humidified atmosphere of 5% $CO_2$, and labeled with 0.04% (w/v) Trypan Blue (Thermo Fisher Scientific) at RT for 5 min. Cardiomyocytes were visualized at 40× magnification (Nikon Eclipse TS100). Cells from 30 fields of view were analyzed per condition. For survival, seven experiments were performed to include a total of the following number of cells per genotype: 7895 (GJA1-20k-V5), 8163 (GJA1-43k-V5), and 8041 (LacZ-V5). For viability, four separate experiments were performed to include a total of the following number of cells per genotype: 4699 (GJA1-20k-V5), 5017 (GJA1-43k-V5), and 4841 (LacZ-V5). Cells that excluded Trypan Blue (TBEs) were considered to have survived. Healthy and viable rod-shaped myocytes (rods) were identified when the length/width ratio was 3:1. Percent survival was calculated as the total number of TBEs divided by the total number of cells (TBEs+nonTBEs), multiplied by 100. Percent viability was calculated as the number of rod shaped TBEs divided by total number of TBEs (rod+contracted cells), multiplied by 100.

Molecular Biology

Full-length and truncated human GJA1 cDNAs (Open Biosystems) were cloned into pDONR/221, and used to generate C-terminal GFP-, mCherry-, V5-, and HA-tagged expression clones as well as adenoviral pDEST vectors, as previously described (see e.g., J. W. Smyth, R. M. Shaw, Autoregulation of connexin43 gap junction formation by internally translated isoforms. Cell reports 5, 611 (Nov. 14, 2013)). Internal methionine start sites were mutagenized to leucine. Mutagenesis was carried out with the QuickChange Lightning Mutagenesis Kit (Agilent) according to manufacturer's instructions. Mutagenesis primers used to remove all six tubulin-interacting (23) residues ($^{239}RV^{240}$ and $^{247}YHAT^{250}$) to generate GJA1-20k-del6 are: 5' AAG GGC GTT AAG GAT AAG GGA AAG AGC GAC CCT AGT GGT GCG CTG AGC 3' (SEQ ID NO: 9), and 5' GCT CAG CGC ACC ACT AGG GTC GCT CTT TCC CTT ATC CTT AAC GCC CTT 3' (SEQ ID NO: 10). All plasmids are available at the nonprofit Addgene repository (http://www.addgene.org/Robin_Shaw/accessed on Apr. 12, 2017). The mito-BFP plasmid was a gift from Dr. Gia Voeltz (Addgene plasmid #49151).

STORM Imaging

Crude mitochondria were plated on 35 mm glass-bottom dishes (MatTek) for 1.5 hours at 4° C. They were fixed with 4% PFA at RT for 10 minutes before blocking and permeabilization for 10 minutes at RT with 1% NGS and 0.5% TritonX-100 in PBS. Primary antibodies were incubated overnight at 4° C.: rabbit anti-Tom20 (1:200; Santa Cruz Biotechnology) and mouse anti-V5 (1:200, Sigma-Aldrich). Secondary detection was carried out for 1 hour at RT using Alexa Fluors (1:500, Thermo Fisher Scientific). Samples were extensively washed and air-dried in the dark at RT. On the day of STORM imaging, freshly made oxygen-scavenging buffer system was added to the mitochondria-containing dishes to enable effective photoswitching. Briefly, 10 mmol/L cysteamine (Sigma-Aldrich) was added to GLOX (0.5 mg/mL glucose oxidase, 40 μg/mL catalase, 10% glucose) in 50 mmol/L Tris buffer (pH8.0) with 10 mmol/L NaCl. All images were collected using a Nikon Eclipse Ti microscope with a ×100/1.49 Apo TIRF objective. The STORM images (signals within 500 nm Z-depth from the coverslips) were acquired using 488 nm and 561 nm lasers from a self-contained 4-line laser module with AOTF, and a high-speed iXon DU897 Ultra EMCCD camera. Fresh STORM imaging buffer was exchanged every hour to maintain photoswitching properties of the sample. The STORM module in Nikon Element software was used to obtain and analyze the images to generate 3-dimensional projections of GJA1-20k-V5/Tom20, LacZ-V5/Tom20, or GJA1-43kV5/Tom20 images at XY-resolution of 10-20 nm, and Z-resolution of 50 nm.

Confocal Fixed and Live-Cell Imaging

All fixed cell and tissue samples were acquired using our Nikon Eclipse Ti imaging system with a ×100/1.49 Apo TIRF objective, a spinning disk confocal unit (Yokogowa CSU-X1) with 486, 561, and 647-nm diode-pumped solid state lasers, and an ORCA-Flash 4.0 Hamamatsu camera (C11440), controlled by NIS Elements software. Live cell imaging was carried out in transiently transfected HeLa cells. Briefly, glass-bottomed dishes were coated with human fibronectin (10 μg/ml, Corning) and 0.1% gelatin (Sigma-Aldrich). HeLa cells (ATCC, CCL-2) were grown on these dishes at 37° C. in a humidified atmosphere of 5% $CO_2$ in fully supplemented media containing DMEM with 10% fetal bovine serum (FBS), nonessential amino acids, sodium pyruvate (Thermo Fisher Scientific), and Mycozap-CL (Lonza). Cells were cotransfected with fluorescently tagged GJA1 isoforms and mito-BFP using Lipofectamine 2000 according to manufacture's instructions (Thermo Fisher Scientific). At 16-24 hours post transfection, cells were immersed in imaging solution containing HBSS supplemented with 10% FBS, and 1× Mycozap-CL. Images were acquired at 37° C. using our Nikon Eclipse Ti imaging system described above. Active mitochondria were labeled by loading cells for 30 min with imaging solution containing 2.5 μM tetramethylrhodamine methyl ester perchlorate (TMRM, Thermo Fisher Scientific).

Mitochondrial Distribution and Morphology Analysis Upon $H_2O_2$ Treatment

HeLa cells were plated on coated glass-bottom dishes, as described above, and transfected with the following plasmids: GST-GFP, GJA1-43k-GFP, and GJA1-20k-GFP. At 24 hours post transfection, samples were treated with 300 μM $H_2O_2$ (Sigma-Aldrich) or PBS in fully supplemented medium for 4 hours. Cells were fixed in 4% PFA (Electron Microscopy Services) in PBS for 20 minutes at RT. Immunolabeling was performed using rabbit anti-Tom20 (1:100, Santa Cruz Biotechnology) and chick anti-GFP (1:500, Abcam). Alexa Fluors (Thermo Fisher Scientific) were used for secondary antibody detection for 1 hour at RT. ProLong Gold Antifade containing DAPI was used to mount samples prior to image acquisition. Using ImageJ (NIH), the peripheral/central fluorescence ratio was determined by dividing peripheral Tom20 signal by that of the perinuclear and Golgi regions. First, each image is background-subtracted using a rolling ball radius of 50 pixels. Thresholding for the inner region of interest (ROI) encompassing the nucleus was set based on ⅙ of the maximal Tom20 intensity of the entire cell. Signal from the nuclear ROI was removed from the cell. The middle ROI (perinuclear/Golgi) boundary was set by expanding the inner ROI by 4 micrometers. Finally, signal density from the remaining outer ROI (periphery) is divided by the sum of that of the inner and middle ROIs to obtain the ratio shown in FIGS. 3 and 4. Percentages of cells with connected mitochondria in FIGS. 3 and 4 were determined by scoring blinded datasets of immunolabeled Tom20 signal from at least 4 experimental replicates.

Electron Microscopy

For transmission electron microscopy (TEM), HeLa cells were transfected with GST-GFP or GJA1-20k-GFP plasmids as described above. Cells were fixed in 2% glutaraldehyde in PBS at RT for 10 minutes, scraped, and pelleted by centrifugation at 4200×g followed by 16,000×g. Pellets were fixed for 2 additional hours, and then post fixed with 1% osmium tetroxide followed by incubation with 3% uranyl acetate. The samples were dehydrated in ethanol, treated with propylene oxide, embedded in Spurr resin (Electron Microscopy Services), and sectioned using an ultramicrotome (UCT, Leica). The sections were then mounted on EM grids and stained with uranyl acetate and lead citrate. Images were acquired using the JEM1200-EX, JEOL microscope equipped with a digital camera (BioScan 600W, Gatan). For immunoelectron microscopy, cells were fixed in 4% formaldehyde and 0.1% glutaraldehyde in PBS at RT for 10 minutes, scraped, and pelleted as described above. Cells were fixed overnight at 4° C. in 4% formaldehyde and 0.1% glutaraldehyde in PBS and thereafter mixed with 1.5% low melting temperature agarose. Small pieces of agarose with embedded cells were incubated overnight in 1.85 M sucrose/20% PVP-10/50 mM Hepes pH 7.4. Each piece was mounted on an aluminum pin and snap frozen in liquid nitrogen. Ultra-thin sections were prepared using a cryo-ultramicrotome (UC6, Leica) with an F6 cryo-attachment and a Diatome cryoimmuno (35°) diamond knife. The sections were incubated with rabbit anti-GFP primary antibody (1:200; Abcam) at 4° C. overnight. The sections were then incubated with secondary antibody conjugated with 10 nm gold particles (1:20; Ted Pella) and imaged as described above. All electron microscopy work was done at the Electron Imaging Center at California NanoSystems Institute, University of California Los Angeles.

Tracking of Mitochondrial Movement

For tracking experiments, mito-BFP signal was tracked every 5 seconds for 5 minutes in cells expressing comparable levels of GST-GFP, GJA1-20k-GFP, or GJA1-20k-del6-GFP at 24 hours post transfection. Fresh imaging solution, containing either 25 µM nocodazole (to disrupt microtubules) or 0.08% DMSO, was added to cells for 45 minutes prior to image acquisition. To determine mitochondrial velocity and displacement, the MTrackJ plugin for ImageJ (NIH) was used to track individual mitochondrion moving toward the cell tip within a 60×60 µm² ROI. For FIG. 4 E to H, a total of 4 separate experiments were performed to include the following number of mitochondrion tracks per condition: 57 (GST+DMSO), 42 (GST+nocodazole), and 84 (GJA1-20k+DMSO), and 59 (GJA1-20k-del6+DMSO).

Statistical Analysis

All quantitative data were expressed as mean+/−s.e.m. and analyzed using Prism 6 software (GraphPad). One-way ANOVA followed by Tukey's post-test was performed for FIG. 1B. Two-way ANOVA followed by Tukey's multiple comparisons test was performed for the remaining quantifications. A P value less than 0.05 was deemed statistically significant. For tracking data in FIG. 4H, histograms of mean velocities of each condition were used for nonlinear Gaussian fitting. Single Gaussian fitting generated the following coefficients of determination ($R^2$) to assess the goodness of fit: 0.9313 (GST control), 0.9452 (GST treated with nocodazole), 0.7776 (GJA1-20k), and 0.8466 (GJA1-20k-del6). Based on these values, data for GJA1-20k and GJA1-20k-del6 were fitted with the sum of two Gaussian distributions to yield $R^2$ values of 0.907 and 0.9745, respectively.

Constructs

All constructs generated in this study are available at the Addgene plasmid repository.

GJA1-20k Isoform Sequence

Figure 5:
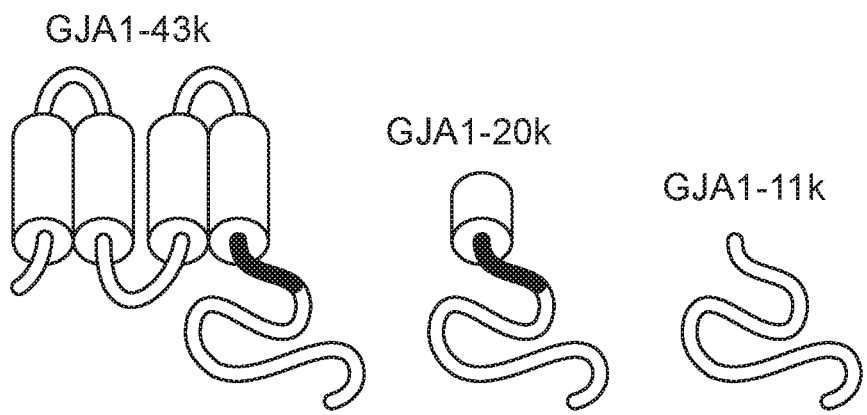
FIG. 5 depicts, in accordance with various embodiments of the invention, GJA1-20k isoform sequence (SEQ ID NO: 1) and GJA1-11k isoform sequence (SEQ ID NO: 11). Bold and underlined sequence is required for mitochondrial targeting. Residues in bold ("RV" and "YHAT") do not cause GJA1-20k to be lost from the mitochondria; instead, they are essential for GJA1-20k to facilitate mitochondrial trafficking and cellular protection.
Figure 6A:
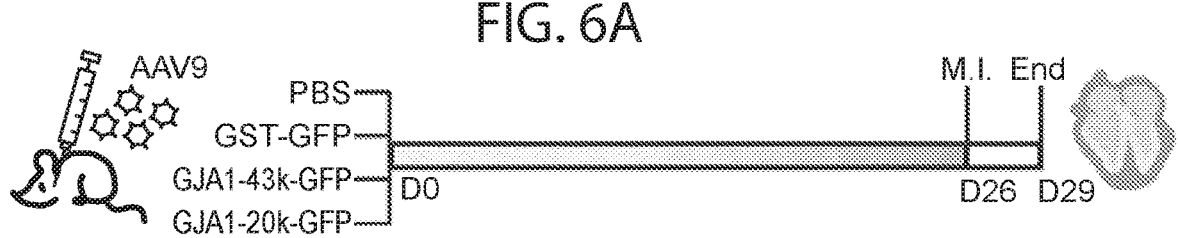
FIGS. 6A-6C depicts, in accordance with various embodiments of the invention, the in vivo cardioprotective effect of GJA1-20k.
Figure 6B:
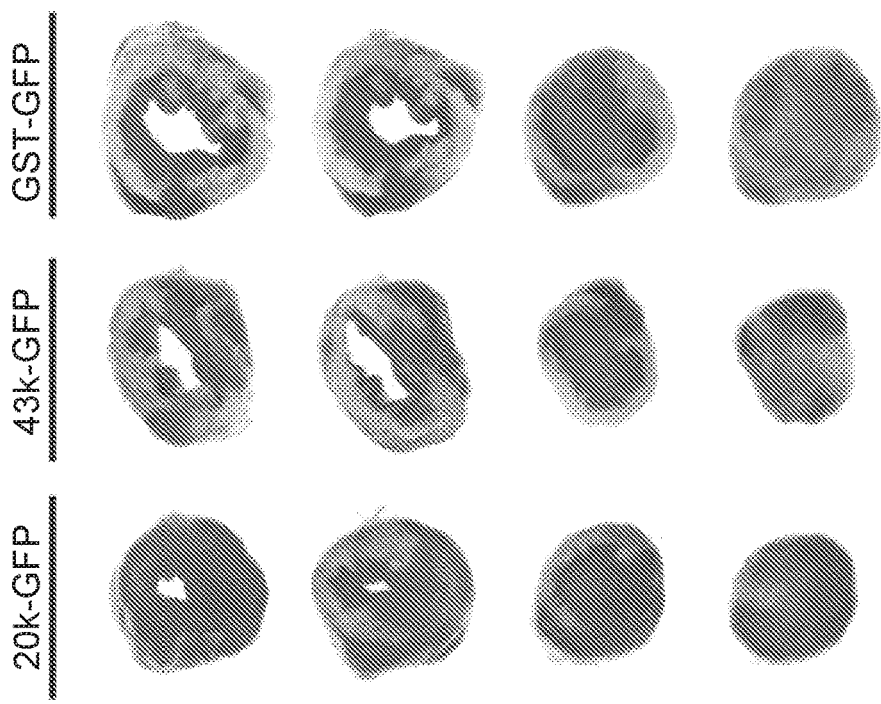
Figure 6C:
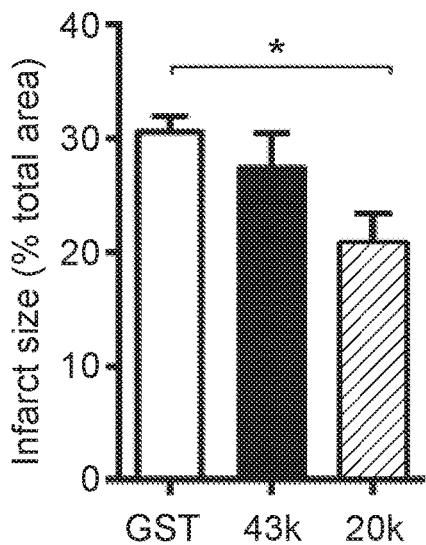
Figure 7A:
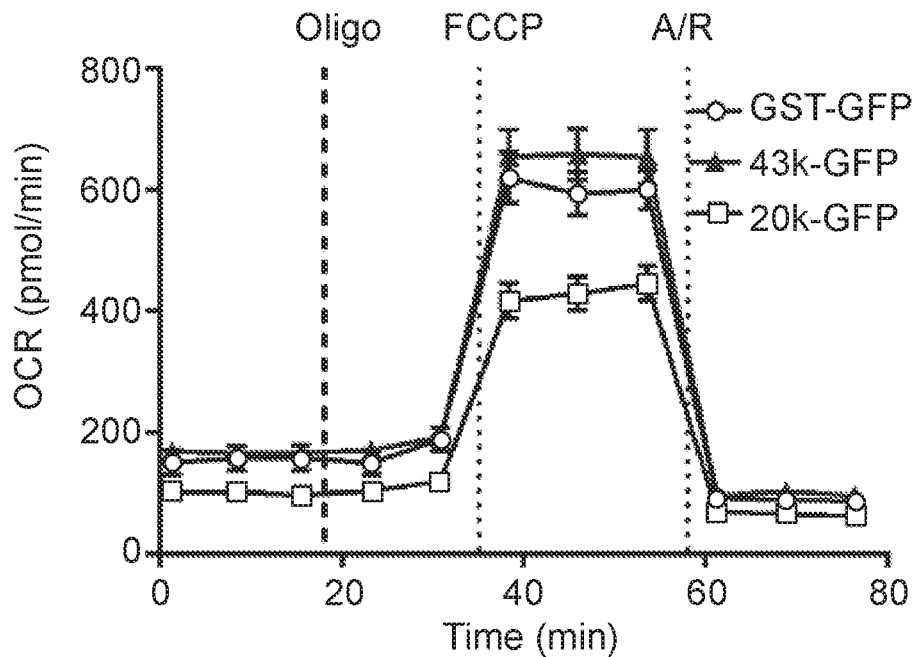
FIGS. 7A-7B depicts, in accordance with various embodiments of the invention, the metabolic mechanisms underlying the cardioprotective action of GJA1-20k.
Figure 7B:
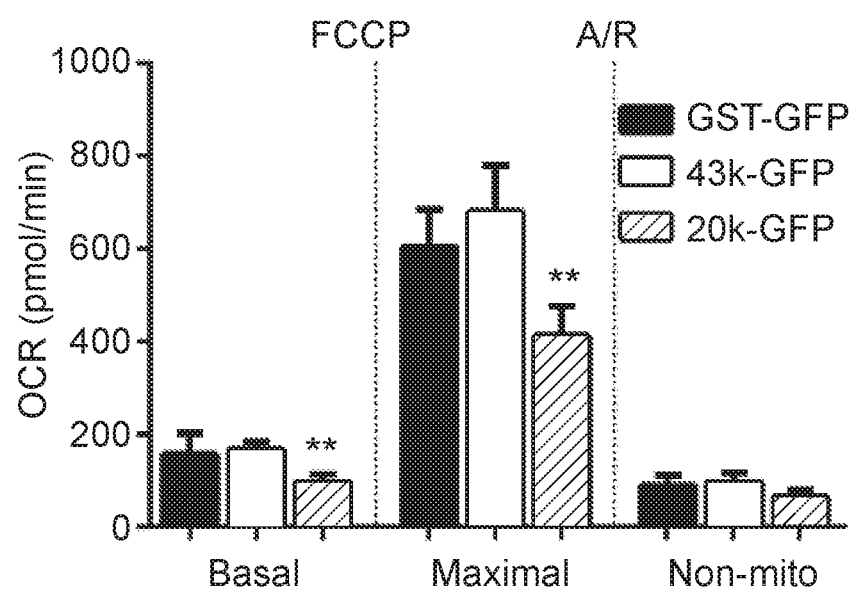

As shown in FIG. 5, one non-limiting example of GJA1-20k (SEQ ID NO: 1) has the sequence:

```
MLVVSLVSLALNIIELFYVFFKGVKDRVKGKSDPYHATSGALSPAKDC

GSQKYAYFNGCSSPTAPLSPMSPPGYKLVTGDRNNSSCRNYNKQASEQ

NWANYSAEQNRMGQAGSTISNSHAQPFDFPDDNQNSKKLAAGHELQPL

AIVDQRPSSRASSRASSRPRPDDLEI.
```

We identified that mitochondrial targeting requires the sequence:

```
                                        (SEQ ID NO: 4)
            KGVKDRVKGKSDPYHATSGALSPAKDC.
```

We further identified that the specific residues "RV" and "YHAT" (red) do not cause GJA1-20k to be lost from the mitochondria. Instead, they are essential for GJA1-20k to facilitate mitochondrial trafficking and cellular protection:

GJA1-11k Isoform Sequence

As shown in FIG. 5, one non-limiting example of GJA1-11k (SEQ ID NO: 11) has the sequence:

```
MSPPGYKLVTGDRNNSSCRNYNKQASEQNWANYSAEQNRMGQAGSTIS

NSHAQPFDFPDDNQNSKKLAAGHELQPLAIVDQRPSSRASSRASSRPR

PDDLEI.
```

Method of Delivery

Plasmid transfection and adenoviral transduction may be used to deliver the isoforms. Also, cell penetrating or cell internalization peptides may be fused with the isoforms for delivery. Non-limiting examples of cell penetrating or cell internalization peptides include: TAT (GRKKRRQRRRPQ—SEQ ID NO: 5); Poly-arginine (RRRRRRRR, D-isomers—SEQ ID NO: 6); and Antennapedia (RQIKIWFQNRRMKWKK—SEQ ID NO: 7). For example, patients experiencing ischemic injury due to trauma or cardiovascular diseases can benefit from the GJA1-20k therapeutic agents. For example, the GJA1-20k isoform tagged with these cell penetrating or cell internalization peptides may be used as injectable or topical agents administered to tissues subjected to ischemic/reperfusion injury (e.g., heart and brain).

Example 2 Cardioprotective Effects of GJA1-20k To determine whether GJA1-20k exerts a cardioprotective action in vivo, the inventors performed permanent Left Anterior Descending (LAD) coronary artery ligation as an experimental infarction in adult mice. Introduction of GJA1-20k was achieved by AAV9-medicated gene transfer using retro-orbital injection four weeks before the ischemic insult (FIG. 1A). GJA1-43k, was found to protect the heart. Compared to a GFP control group, myocardial infarct size in GJA1-20k treated hearts is reduced by 30% at 72 hours post LAD ligation (FIGS. 1B and 1C), indicating that GJA1-20k is capable of limiting damage induced by acute ischemia and infarction, improving heart muscle survival. Without being bound to any particular theory, improved acute heart muscle survival will lead to long term improved mortality from heart failure.

The metabolic mechanisms underlying the cardioprotective action of GJA1-20k were further explored. Cardiomyocytes were isolated from mice previously injected with AAV9 virus encoding GST-GFP, 43k-GFP and 20k GFP. The Seahorse assay was used to measure metabolic function in the isolated cardiomyocytes. The inventors found that basal mitochondria-dependent oxygen consumption and maximal respiratory capacity are markedly reduced by GJA1-20k, unlike GFP or GJA1-43k controls. Without being bound to any particular theory, the data indicate that GJA1-20k induces mitochondrial metabolic quiescence, which preserves the health of cardiomyocytes by lowering energy output and improves survival when subjected to ischemic injury.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method of treating, reducing the likelihood of having, reducing the severity of and/or slowing the progression of a condition in a subject, comprising: providing a polypeptide consisting of GJA1-20k polypeptide having SEQ ID NOs: 1, 2 or 3, or a polypeptide consisting of the GJA1-20k polypeptide having SEQ ID NOs: 1, 2 or 3 fused to a cell penetrating peptide (CPP), or a gene expression vector comprising a sequence encoding the polypeptide consisting of GJA1-20k polypeptide having SEQ ID NOs: 1, 2 or 3, wherein the gene expression vector is configured for expressing the polypeptide consisting of GJA1-20k polypeptide having SEQ ID NOs: 1, 2 or 3; and administering a therapeutically effective amount of the polypeptide consisting of GJA1-20k polypeptide having SEQ ID NOs: 1, 2 or 3, the polypeptide consisting of the GJA1-20k polypeptide having SEQ ID NOs: 1, 2 or 3 fused to a cell penetrating peptide (CPP), the gene expression vector comprising the sequence encoding the polypeptide consisting of GJA1-20k polypeptide having SEQ ID NOs: 1, 2 or 3, to the subject, thereby treating, reducing the likelihood of having, reducing the severity of and/or slowing the progression of the condition in the subject, wherein the condition is metabolic stress, ischemia, or both.

2. The method of claim 1, wherein the subject is one who has had a previous myocardial infarction.

3. The method of claim 1, wherein the administration of the polypeptide consisting of the GJA1-20k polypeptide or the GJA1-20k polypeptide fused to the CPP results in a cardioprotective effect.

4. The method of claim 3, wherein the cardioprotective effect comprises a reduction in basal mitochondrial dependent oxygen consumption and maximal respiratory capacity.

5. The method of claim 1, wherein the administration of the gene expression vector comprising the sequence encoding the polypeptide consisting of GJA1-20k polypeptide results in a cardioprotective effect.

6. The method of claim 5, wherein the cardioprotective effect comprises a reduction in basal mitochondrial dependent oxygen consumption and maximal respiratory capacity.

7. A method of protecting a cell from metabolic stress, comprising:
providing
a polypeptide consisting of GJA1-20k polypeptide having SEQ ID NOs: 1, 2 or 3, or
a polypeptide consisting of the GJA1-20k polypeptide having SEQ ID NOs: 1, 2 or 3 fused to a cell penetrating peptide (CPP), or
a gene expression vector comprising a sequence encoding the polypeptide consisting of GJA1-20k polypeptide having SEQ ID NOs: 1, 2 or 3, wherein the gene expression vector is configured for expressing the GJA1-20k polypeptide having SEQ ID NOs:1, 2 or 3; and contacting the cell with
the polypeptide consisting of GJA1-20k polypeptide having SEQ ID NOs: 1, 2 or 3, or
polypeptide consisting of the GJA1-20k polypeptide having SEQ ID NOs: 1, 2 or 3 fused to a cell penetrating peptide (CPP), or
the gene expression vector comprising the sequence encoding the polypeptide consisting of GJA1-20k polypeptide having SEQ ID NOs: 1, 2 or 3, thereby protecting the cell from metabolic stress.

8. The method of claim 7, wherein contacting the cell with the GJA1-20k polypeptide or the GJA1-20k polypeptide fused to a CPP results in a reduction in basal mitochondrial dependent oxygen consumption and maximal respiratory capacity.

9. The method of claim 7, wherein contacting the cell with the gene expression vector comprising the sequence encoding the polypeptide consisting of GJA1-20k polypeptide having SEQ ID NOs: 1, 2 or 3 results in a reduction in basal mitochondrial dependent oxygen consumption and maximal respiratory capacity.

10. The method of claim 1, wherein the subject has or is having a myocardial infarction, open heart surgery, cardiopulmonary bypass, coronary artery reperfusion, stroke, ischemic stroke, or nephrotoxicity.

11. The method of claim 1, wherein treating, reducing the likelihood of having, reducing the severity of and/or slowing the progression of metabolic stress or ischemia results in treating, reducing the likelihood of having, reducing the severity of and/or slowing the progression of reperfusion injury in a subject who underwent or is undergoing reperfusion.

12. The method of claim 1, wherein the polypeptide consisting of the GJA1-20k polypeptide, polypeptide consisting of the GJA1-20k polypeptide fused to the CPP, or the gene expression vector is provided in a composition.

13. The method of claim 7, wherein the polypeptide consisting of the GJA1-20k polypeptide, polypeptide consisting of the GJA1-20k polypeptide fused to the CPP, or the gene expression vector is provided in a composition.

* * * * *

SEQUENCE LISTING

```
<160> NUMBER OF SEQ ID NOS: 11

<210> SEQ ID NO 1
<211> LENGTH: 170
<212> TYPE: PRT
<213> ORGANISM: Homo sapiens

<400> SEQUENCE: 1

Met Leu Val Val Ser Leu Val Ser Leu Ala Leu Asn Ile Ile Glu Leu
1               5                   10                  15

Phe Tyr Val Phe Phe Lys Gly Val Lys Asp Arg Val Lys Gly Lys Ser
            20                  25                  30

Asp Pro Tyr His Ala Thr Ser Gly Ala Leu Ser Pro Ala Lys Asp Cys
```

```
                35                  40                  45
Gly Ser Gln Lys Tyr Ala Tyr Phe Asn Gly Cys Ser Ser Pro Thr Ala
 50                  55                  60

Pro Leu Ser Pro Met Ser Pro Pro Gly Tyr Lys Leu Val Thr Gly Asp
 65                  70                  75                  80

Arg Asn Asn Ser Ser Cys Arg Asn Tyr Asn Lys Gln Ala Ser Glu Gln
                 85                  90                  95

Asn Trp Ala Asn Tyr Ser Ala Glu Gln Asn Arg Met Gly Gln Ala Gly
                100                 105                 110

Ser Thr Ile Ser Asn Ser His Ala Gln Pro Phe Asp Phe Pro Asp Asp
                115                 120                 125

Asn Gln Asn Ser Lys Lys Leu Ala Ala Gly His Glu Leu Gln Pro Leu
                130                 135                 140

Ala Ile Val Asp Gln Arg Pro Ser Ser Arg Ala Ser Ser Arg Ala Ser
145                 150                 155                 160

Ser Arg Pro Arg Pro Asp Asp Leu Glu Ile
                165                 170

<210> SEQ ID NO 2
<211> LENGTH: 170
<212> TYPE: PRT
<213> ORGANISM: Mus musculus

<400> SEQUENCE: 2

Met Leu Val Val Ser Leu Val Ser Leu Ala Leu Asn Ile Ile Glu Leu
 1               5                  10                  15

Phe Tyr Val Phe Phe Lys Gly Val Lys Asp Arg Val Lys Gly Arg Ser
                 20                  25                  30

Asp Pro Tyr His Ala Thr Thr Gly Pro Leu Ser Pro Ser Lys Asp Cys
                 35                  40                  45

Gly Ser Pro Lys Tyr Ala Tyr Phe Asn Gly Cys Ser Ser Pro Thr Ala
 50                  55                  60

Pro Leu Ser Pro Met Ser Pro Pro Gly Tyr Lys Leu Val Thr Gly Asp
 65                  70                  75                  80

Arg Asn Asn Ser Ser Cys Arg Asn Tyr Asn Lys Gln Ala Ser Glu Gln
                 85                  90                  95

Asn Trp Ala Asn Tyr Ser Ala Glu Gln Asn Arg Met Gly Gln Ala Gly
                100                 105                 110

Ser Thr Ile Ser Asn Ser His Ala Gln Pro Phe Asp Phe Pro Asp Asp
                115                 120                 125

Ser Gln Asn Ala Lys Lys Val Ala Ala Gly His Glu Leu Gln Pro Leu
                130                 135                 140

Ala Ile Val Asp Gln Arg Pro Ser Ser Arg Ala Ser Ser Arg Ala Ser
145                 150                 155                 160

Ser Arg Pro Arg Pro Asp Asp Leu Glu Ile
                165                 170

<210> SEQ ID NO 3
<211> LENGTH: 170
<212> TYPE: PRT
<213> ORGANISM: Rattus norvegicus

<400> SEQUENCE: 3

Met Leu Val Val Ser Leu Val Ser Leu Ala Leu Asn Ile Ile Glu Leu
 1               5                  10                  15

Phe Tyr Val Phe Phe Lys Gly Val Lys Asp Arg Val Lys Gly Arg Ser
```

```
                    20                  25                  30
Asp Pro Tyr His Ala Thr Thr Gly Pro Leu Ser Pro Ser Lys Asp Cys
                35                  40                  45

Gly Ser Pro Lys Tyr Ala Tyr Phe Asn Gly Cys Ser Ser Pro Thr Ala
         50                  55                  60

Pro Leu Ser Pro Met Ser Pro Pro Gly Tyr Lys Leu Val Thr Gly Asp
 65                  70                  75                  80

Arg Asn Asn Ser Ser Cys Arg Asn Tyr Asn Lys Gln Ala Ser Glu Gln
                 85                  90                  95

Asn Trp Ala Asn Tyr Ser Ala Glu Gln Asn Arg Met Gly Gln Ala Gly
                100                 105                 110

Ser Thr Ile Ser Asn Ser His Ala Gln Pro Phe Asp Phe Pro Asp Asp
            115                 120                 125

Asn Gln Asn Ala Lys Lys Val Ala Ala Gly His Glu Leu Gln Pro Leu
        130                 135                 140

Ala Ile Val Asp Gln Arg Pro Ser Ser Arg Ala Ser Ser Arg Ala Ser
145                 150                 155                 160

Ser Arg Pro Arg Pro Asp Asp Leu Glu Ile
                165                 170

<210> SEQ ID NO 4
<211> LENGTH: 27
<212> TYPE: PRT
<213> ORGANISM: Homo sapiens

<400> SEQUENCE: 4

Lys Gly Val Lys Asp Arg Val Lys Gly Lys Ser Asp Pro Tyr His Ala
 1               5                  10                  15

Thr Ser Gly Ala Leu Ser Pro Ala Lys Asp Cys
            20                  25

<210> SEQ ID NO 5
<211> LENGTH: 21
<212> TYPE: PRT
<213> ORGANISM: Homo sapiens

<400> SEQUENCE: 5

Lys Gly Val Lys Asp Lys Gly Lys Ser Asp Pro Ser Gly Ala Leu Ser
 1               5                  10                  15

Pro Ala Lys Asp Cys
            20

<210> SEQ ID NO 6
<211> LENGTH: 12
<212> TYPE: PRT
<213> ORGANISM: Artificial Sequence
<220> FEATURE:
<223> OTHER INFORMATION: Synthetic construct

<400> SEQUENCE: 6

Gly Arg Lys Lys Arg Arg Gln Arg Arg Pro Gln
 1               5                  10

<210> SEQ ID NO 7
<211> LENGTH: 8
<212> TYPE: PRT
<213> ORGANISM: Artificial Sequence
<220> FEATURE:
<223> OTHER INFORMATION: Synthetic construct

<400> SEQUENCE: 7
```

```
Arg Arg Arg Arg Arg Arg Arg Arg
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic construct

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 48
<212> TYPE: DNA
<213> ORGANISM: Artificial Sequence
<220> FEATURE:
<223> OTHER INFORMATION: Synthetic construct

<400> SEQUENCE: 9
aagggcgtta aggataaggg aaagagcgac cctagtggtg cgctgagc              48

<210> SEQ ID NO 10
<211> LENGTH: 48
<212> TYPE: DNA
<213> ORGANISM: Artificial Sequence
<220> FEATURE:
<223> OTHER INFORMATION: Synthetic construct

<400> SEQUENCE: 10
gctcagcgca ccactagggt cgctctttcc cttatcctta acgcccctt             48

<210> SEQ ID NO 11
<211> LENGTH: 102
<212> TYPE: PRT
<213> ORGANISM: Homo sapiens

<400> SEQUENCE: 11

Met Ser Pro Pro Gly Tyr Lys Leu Val Thr Gly Asp Arg Asn Asn Ser
1               5                   10                  15

Ser Cys Arg Asn Tyr Asn Lys Gln Ala Ser Glu Gln Asn Trp Ala Asn
                20                  25                  30

Tyr Ser Ala Glu Gln Asn Arg Met Gly Gln Ala Gly Ser Thr Ile Ser
            35                  40                  45

Asn Ser His Ala Gln Pro Phe Asp Phe Pro Asp Asn Gln Asn Ser
        50                  55                  60

Lys Lys Leu Ala Ala Gly His Glu Leu Gln Pro Leu Ala Ile Val Asp
65                  70                  75                  80

Gln Arg Pro Ser Ser Arg Ala Ser Ser Arg Ala Ser Ser Arg Pro Arg
                85                  90                  95

Pro Asp Asp Leu Glu Ile
            100
```